US012810421B2

(12) United States Patent
Lin et al.

(10) Patent No.: US 12,810,421 B2
(45) Date of Patent: Nov. 24, 2026

(54) REAGENT AND KIT FOR IDENTIFYING AND DIAGNOSIS OCULAR SURFACE DISEASE (OSD) AND USE THEREOF

(71) Applicant: Chung Shan Medical University, Taichung City (TW)

(72) Inventors: Pei-Cheng Lin, Taichung City (TW); Han-Hsin Chang, Taichung City (TW); Kai-Wen Chen, Taichung City (TW); Meng-Tien Hsieh, Taichung City (TW); Tsung-Han Lu, Taichung City (TW)

(73) Assignee: Chung Shan Medical University, Taichung City (TW)

( * ) Notice: Subject to any disclaimer, the term of this patent is extended or adjusted under 35 U.S.C. 154(b) by 218 days.

(21) Appl. No.: 18/747,027

(22) Filed: Jun. 18, 2024

(65) Prior Publication Data

US 2025/0384550 A1 Dec. 18, 2025

Related U.S. Application Data

(60) Provisional application No. 63/507,159, filed on Jun. 9, 2023.

(51) Int. Cl.
*G06T 7/00* (2017.01)
*G01N 33/487* (2006.01)

(52) U.S. Cl.
CPC ......... *G06T 7/0012* (2013.01); *G01N 33/487* (2013.01); *G06T 2207/30041* (2013.01)

(58) Field of Classification Search
CPC ........ G06T 7/0012; G06T 2207/30041; G01N 33/487
USPC .......................................................... 382/128
See application file for complete search history.

(56) References Cited

U.S. PATENT DOCUMENTS

| | | | | |
|---|---|---|---|---|
| 2014/0275124 A1* | 9/2014 | Rogosnitzky | ........ | A61K 31/519 514/262.1 |
| 2022/0011291 A1* | 1/2022 | Shafiee | ................ | G01N 33/487 |
| 2023/0233493 A1* | 7/2023 | Joshi | .................... | A61K 9/0048 514/613 |

OTHER PUBLICATIONS

Kevin Kai-WenChen1, SophieMeng-TienHsieh1, Han-Hsin Chang2,andDavid Pei-Cheng Lin (Diagnosis of Photokeratitis by Tear Ferning Using a Novel Set of SK grading criteria in a UVB-Induced Mouse Model). Published Jun. 2023 in Translational Vision Science and Technology) (Year: 2023).*

* cited by examiner

*Primary Examiner* — Stephen P Coleman
(74) *Attorney, Agent, or Firm* — MUNCY, GEISSLER, OLDS & LOWE, P.C.

(57) ABSTRACT

The invention relates to a novel method for precise and early diagnosis to facilitate in time intervention for ocular surface disease (OSD). Therefore, the method is potentially useful for ocular surface disease (OSD) diagnosis in the clinical settings.

10 Claims, 30 Drawing Sheets

REAGENT AND KIT FOR IDENTIFYING AND DIAGNOSIS OCULAR SURFACE DISEASE (OSD) AND USE THEREOF

CROSS-REFERENCE TO RELATED APPLICATIONS

This application claims priority in U.S. Provisional Patent Application No. 63/507,159, filed Jun. 9, 2023, which is incorporated by reference in its entirety herein.

FIELD OF THE INVENTION

The invention relates to a new method (TF test) for precise and early diagnosis to facilitate in time intervention for ocular surface disease (OSD). The TF test was proven to have a capacity to distinguish the ocular surface disease (OSD) from the normal status at an early stage by using the SK grading criteria. It is therefore potentially useful for ocular surface disease (OSD) diagnosis in the clinical settings.

BACKGROUND OF THE INVENTION

Ocular surface disease represents a spectrum of disorders that affect the surface of the eyes. The ocular surface comprises the cornea, conjunctiva, eyelids and lacrimal glands and any disorder in these structures can be classified as an ocular surface disorder (OSD). The tear film, a thin moist layer covering the cornea, plays an important role on the ocular surface. It not only has an immune protective effect, but also provides nutrients to the cornea. Therefore, a close relationship exists between the status of tear film and the health of cornea.

Different types of ocular surface disease may have different tear compositions caused by various pathophysiologic alterations. For example, the TFOS DEWS verified tear hyperosmolarity, resulted from the disorder of tear film homeostasis, as the central symptom of DED. The loss of tear film homeostasis may reveal changes in the chemical composition and functionality of tears.

Given that the quality and quantity of tear film are crucial for ocular health, the ways to examine these tear characteristics are pivotal for ophthalmic diagnosis.

Dry eye syndrome is one of the most common ocular surface diseases, with incidence ranging from 5.7% to 21.6%. Symptoms of dry eye and ocular surface disease include sensation of dryness, redness, tearing, irritation, burning, foreign body sensation, light sensitivity and intermittent blurred vision. By contrast, OSD also includes conditions like blepharitis and meibomian gland dysfunction (MDG), allergic eye diseases (AED), chemical and thermal burns and so on. Ocular surface diseases can severely affect eyesight and quality of life, and in severe cases, cause blindness.

For example, ultraviolet radiation (UVR) has been known to cause photothermal and photomechanical damages, including cellular apoptosis, DNA damage, and detrimental accumulation of reactive free radicals. The scenario may be referred as photokeratitis to describe the acute reactions to UVR-induced "burns". The most reported cases of photokeratitis are "snow blindness" and "welder's flash". The snow blindness occurs from excessive UVB irradiation under naturally high-reflective environments. On the other hand, the welder's flash results from exposure to artificial UVB (and sometimes UVC), such as those from a welder's arc.

The earliest symptoms of photokeratitis emerge as a gritty ocular sensation, followed by photophobia and tearing. These initial symptoms are caused by the loss and damage of cornea epithelial cells on the superficial ocular surface. This leads to corneal edema, resulting in haze and vision impairment. Further exposure to UVR would cause epithelial exfoliation and severe pain. Furthermore, UVB irradiation can induce inflammatory responses, which are regarded as the key mechanisms in photokeratitis.

Early photokeratitis and dry eye share some common symptoms such as tearing, itchy sensation, and ocular surface redness and swelling. Also, allergic conjunctivitis shares similar symptoms at the early stage, which is a challenge for differential diagnosis. Incorrect management for these diseases, for example between dry eye and allergic conjunctivitis at early stages, may lead to worsen pathogenetic aftermath. Nevertheless, the current clinical routine tests, such as tear volume (TV), tear film break up time (TBUT) and cornea staining, have shown weak correlation between sign and symptoms to not totally meet the demand for early and precise diagnosis.

On the other side, the methods also include slit-lamp examination, corneal fluorescein staining, ocular ultrasound and visual acuity testing for diagnosis of photokeratitis. For these abovementioned methods to be helpful, the photokeratitis status is already at certain stages later than the initiation period.

Other assessments such as in vivo confocal microscopy (IVCM) and osmolarity test demand either substantial time, expensive instruments, or personnel skills for completion.

In other words, though the prevalence of OSD is quite high, unfortunately, cases often go undiagnosed or undertreated, due to a lack of early understanding of symptoms, and inaccurate evaluation at early stages.

SUMMARY OF THE INVENTION

An object of the invention is to provide a quick, easy to perform, reproducible, and cost-effective measurement for early and differential diagnosis of OSD, which would be more acceptable in clinical settings.

Another aspect of the present invention provides cultivation of novel, easy to perform, and capable early diagnostic method, which is advantageous for diagnosis of early photokeratitis and dry eye.

The tear ferning (TF) test is known as a quick, simple, and inexpensive test for tear sample assessment. It is performed by putting a drop of tear sample on a glass slide, allowed for air dry in order to form the TF patterns. The previous studies have shown good sensitivity, specificity and repeatability using the TF test. In our previous study, the mouse TF test protocol has been established by using wash solution for collection of a small amount of tear sample, which potentially may be applicable to assess clinical photokeratitis at the early stage.

To develop TF as a novel diagnostic test, we investigated whether the TF patterns can be distinguished between normal and photokeratitis status in a mouse UVB-induced model, by using both the Masmali and a Sophie-Kevin (SK) grading criteria. To further validate the TF test, other indicators commonly used for ocular surface diagnosis were correlated with the TF grades.

BRIEF DESCRIPTION OF THE DRAWINGS

The drawings described herein are for illustration purposes only and are not intended to limit the scope of the present teachings in any way.

FIGS. 3A and 3B, without UVB damage; 3C and 3D, with UVB damage of photokeratitis model.

(FIG. 6A): $r=-0.702$, $p=0.0001$: (FIG. 6B): $r=-0.878$, $p<0.0001$.

FIGS. 9A, 9B, and 9C depict tear crystallization in the control group of aqueous-deficient dry eye (ADDE) model, while FIGS. 9D, 9E, and 9F represent tear crystallization in the injury group. FIGS. 9G, H, and I correspond to the sham surgery group.

FIGS. 13A, 13B, and 13C depict tear crystallization in the control group of evaporative dry eye (EDE) model, while FIGS. 13D, 13E, and 13F represent tear crystallization in the injury group.

DETAILED DESCRIPTION OF THE INVENTION

Figure 1:
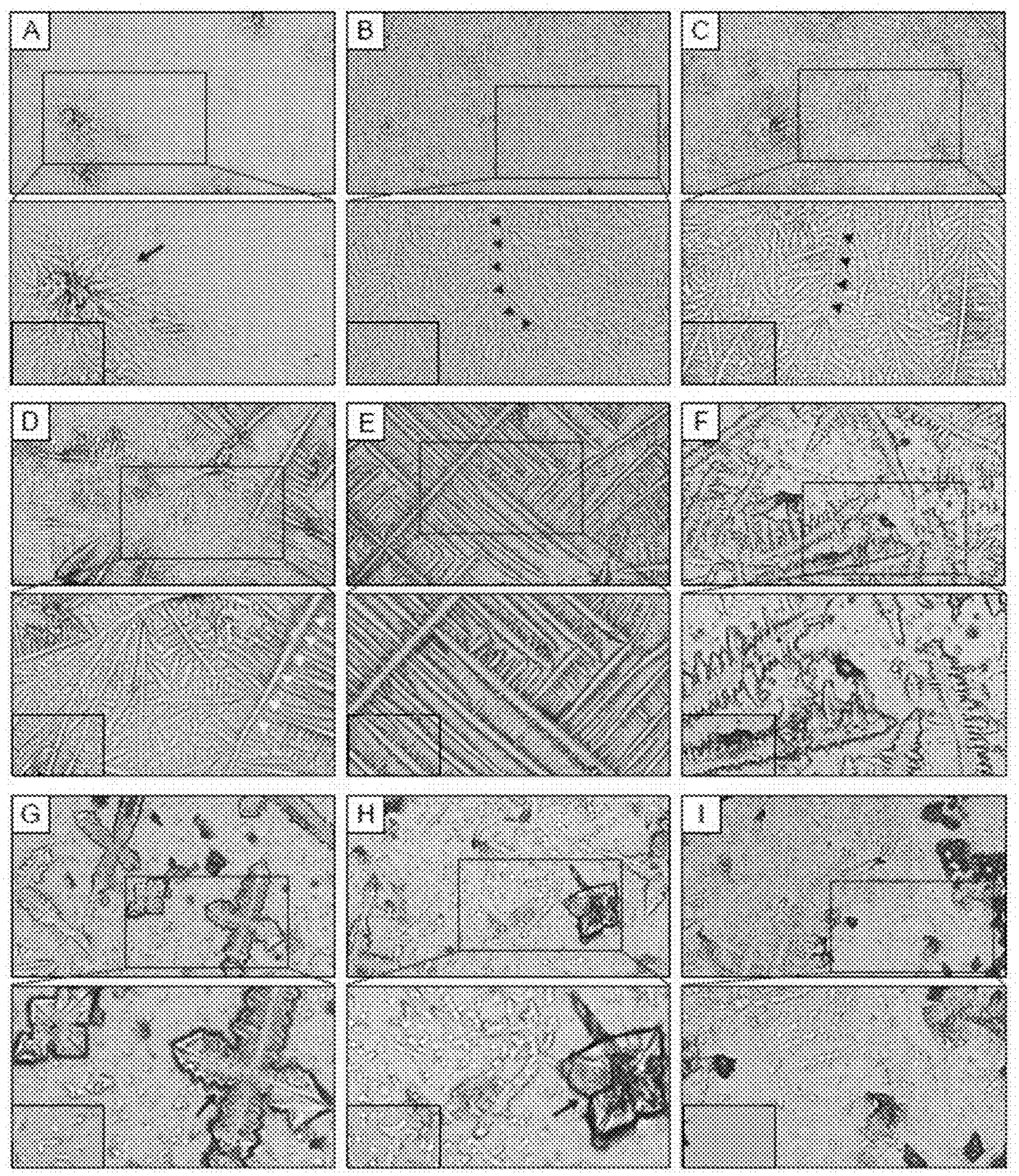
FIG. 1A-1I depict that demonstration of the SK grading criteria for mouse TF. The black boxed areas are magnified and put beneath each grade photo. The inter-crystal spaces of each magnified photo were painted in orange and represented by the black boxed areas on the lower left corner. The black arrows in grade 0, 3 and 3.5 of FIG. 1A, 1G, 1H indicated the snowflake, the cross shape, and the square-like patterns, respectively. The black triangles in grade 0.5 of FIG. 1B, the black triangles in grade 1 of FIG. 1C, and the light-gray triangles in grade 1.5 of FIG. 1D indicated the trunk crystals from finer to coarser, as the grade scales were increased. The dark-gray right angle marks in grade 2 of FIG. 1E indicated the intersection of TF crystals at right angle. All the original photos were magnified at 100×.

The following description is merely exemplary in nature and is in no way intended to limit the present teachings, application, of uses.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Statistical Analysis

The data are presented as the means±standard error of the means (SEMs) and compared with Mann Whitney U test. The Pearson correlation was used to depict relationship among the obtained data. Correlation coefficients was considered very weak (0.00-0.19), weak (0.20-0.39), moderate (0.40-0.59), strong (0.60-0.79), and very strong (0.80-1.00). All statistical analyses were performed by using GraphPad Prism 9 software (GraphPad Software, San Diego, CA, USA)

Example 1

Ocular Surface Disease (OSD) Model

A total of twelve 8-week-old female Institute of Cancer Research (ICR) mice were purchased from BioLASCO Taiwan Co., Ltd, Taipei, Taiwan. The mice were fed ad libitum and kept at 20° C. to 24° C. with 50% to 55% humidity under a 12 h: 12 h light-dark cycle. Only mice without anomalies of the anterior eye (cornea, anterior chamber, iris, or lens) were included in the experiments. All procedures involving mice were reviewed and approved by the Institutional Animal Care and Use Committee of Chung Shan Medical University and were performed in accordance with the Association for Research in Vision and Ophthalmology (ARVO) Resolution on the Use of Animals in Ophthalmic and Vision Research.

Photokeratitis Model

The mice were randomly divided into two groups: blank control (blank) and UVB-damaged (damage). Each group contained six mice. After the mice being anesthetized with 2.5% Avertin (Sigma-Aldrich, St. Louis, MO) at 400 mg/kg by intraperitoneal injection, the eyes of the damage group were directly exposed to UVB light (LF-206LS: UVItec Limited, England) in a darkroom once daily. The UVB source was set at 8 mW/cm2 with exposure time for 90 seconds to reach a total amount of 0.72 J/cm2/day, during a 10-day (days 1 to 10) experiment period. The UVB light wavelength ranged between 280 nm and 320 nm with a peak at 312 nm, which was confirmed with a UV detector (VLX-3W: Vilber Lourmat). After the UVB irradiation, the mice were transferred to their original cages set under normal room light. The mice of the blank group were treated in a similar manner except the exposure to UVB.

Aqueous-Deficient Dry Eye (ADDE) Model

The mice for external lacrimal gland excision-induced injury were divided into three groups: the control group, injury group, and sham surgery group. Testing commenced seven days after the surgery: The sham surgery group was included to verify that the observed effects were not solely due to the surgery or the long-acting anesthesia. In the sham surgery group, a small piece of adipose tissue was excised instead of the entire external lacrimal gland, distinguishing it from the injury group.

Evaporative Dry Eye (EDE) Model

Mice were immobilized in front of a fan to induce wind-induced ocular surface injury. The abovementioned injury experiment was performed for five hours per day over 10 consecutive days.

Mucin-Deficient Dry Eye Model

N-acetylcysteine (NAC) is a mucolytic agent that disrupts disulfide bonds in mucoproteins, converting them into low-molecular-weight mucoprotein molecules, thereby destabilizing the mucus layer. NAC powder is dissolved in sterile saline to prepare a concentration of 10% N-Acetylcysteine (NAC) eye drops. Then drop 5 μL NAC solution onto the ocular surface of each eye for four times per day over 10 consecutive days 10 days.

Example 2

Data Collection Assessment Schedule

Before every measurement, the mice were anesthetized with intraperitoneal 2.5% Avertin injection (Sigma-Aldrich, St. Louis, MO) at 400 mg/kg. The TF tests were conducted on days 0, 3, 4, 5, 7, 9, and 10. To avoid potential interference with the TF tests, assessments of TV and TBUT were performed on day 11. The cornea stain photography was conducted on day 12. Measurements were performed and the data were obtained from both the right and the left eyes.

Example 3

Measurement of TV and TBUT for OSD Model

The TV was measured under anesthetized condition with a tear test strip (Advantech test paper, Tokyo Roshi Kaisha, Japan) of 1-mm width. The lower eyelid was pulled down slightly and a strip was placed on the palpebral conjunctiva for 20 seconds. The moistened length of the strip was measured in millimeters. The TV test was repeated three times for each eye with the average taken as the results.

The TBUT assessments were performed with instilling 5 μL of 1% fluorescein on the center cornea using a micropipette. The eyelid closures were manually aided for three times, and the ocular surface was examined under a dissection stereoscope (Stemi SV 11: Carl Zeiss, Germany) with an illuminating system (HBO 100; Carl Zeiss, Germany). The appearance of fluorescein in the tear film was observed under cobalt blue light. The time when the first dark spot emerged on the cornea surface was recorded. The experiment was repeated three times for each eye to obtain an average value To investigate TV and TBUT after UVB exposure for 10 days, the tear strip test and fluorescein instillation were performed in this embodiment.

Figure 2:
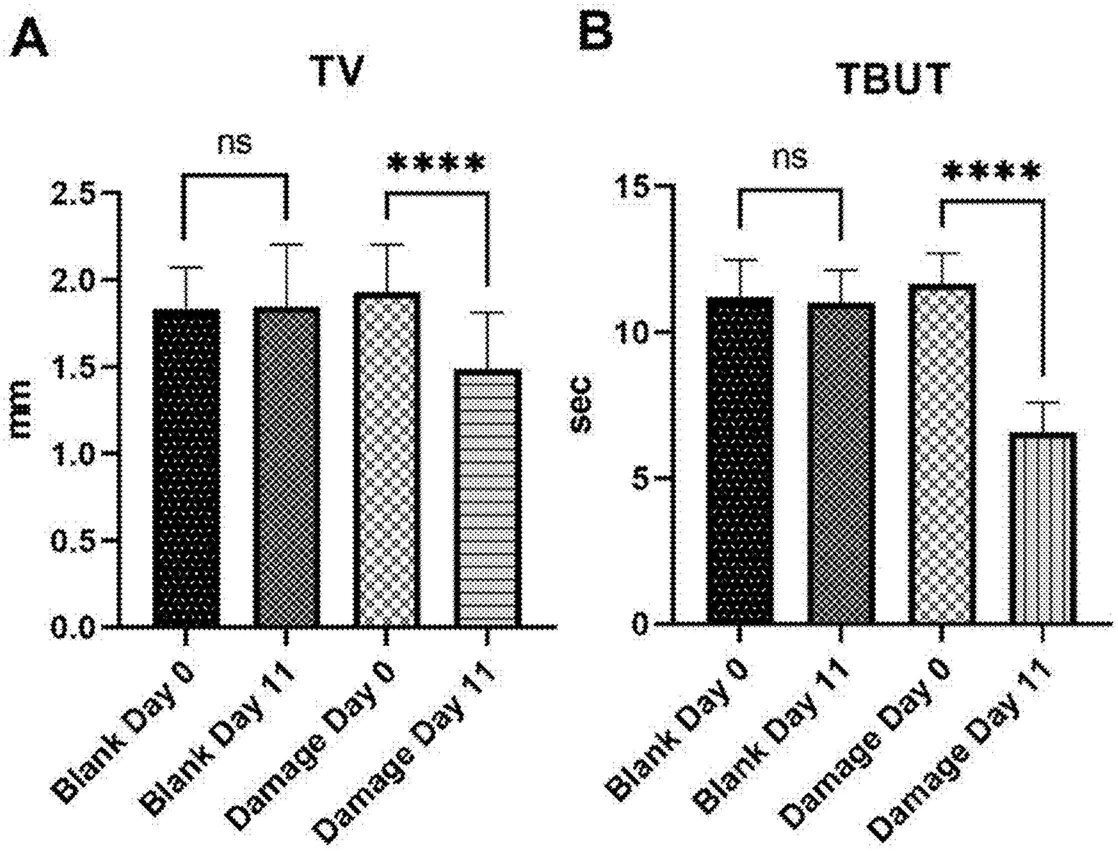
FIG. 2 depict that the tear volume (TV) and tear film break-up time (TBUT) on day's 0 and 11 with or without UVB damage of photokeratitis model. mm, millimeter: sec, second: ns, non-significant. **** $p<0.0001$, by Mann-Whitney U test: n=12 for both the blank and the damage groups.

The results of photokeratitis model showed that the TV was significantly reduced in the damage group, and there was no significant difference in the blank group after 10 days (FIG. 2A). Similarly, the TBUT in the damage group decreased significantly, in contrast to the no difference in the blank group after 10 days (FIG. 2B).

Figure 7:
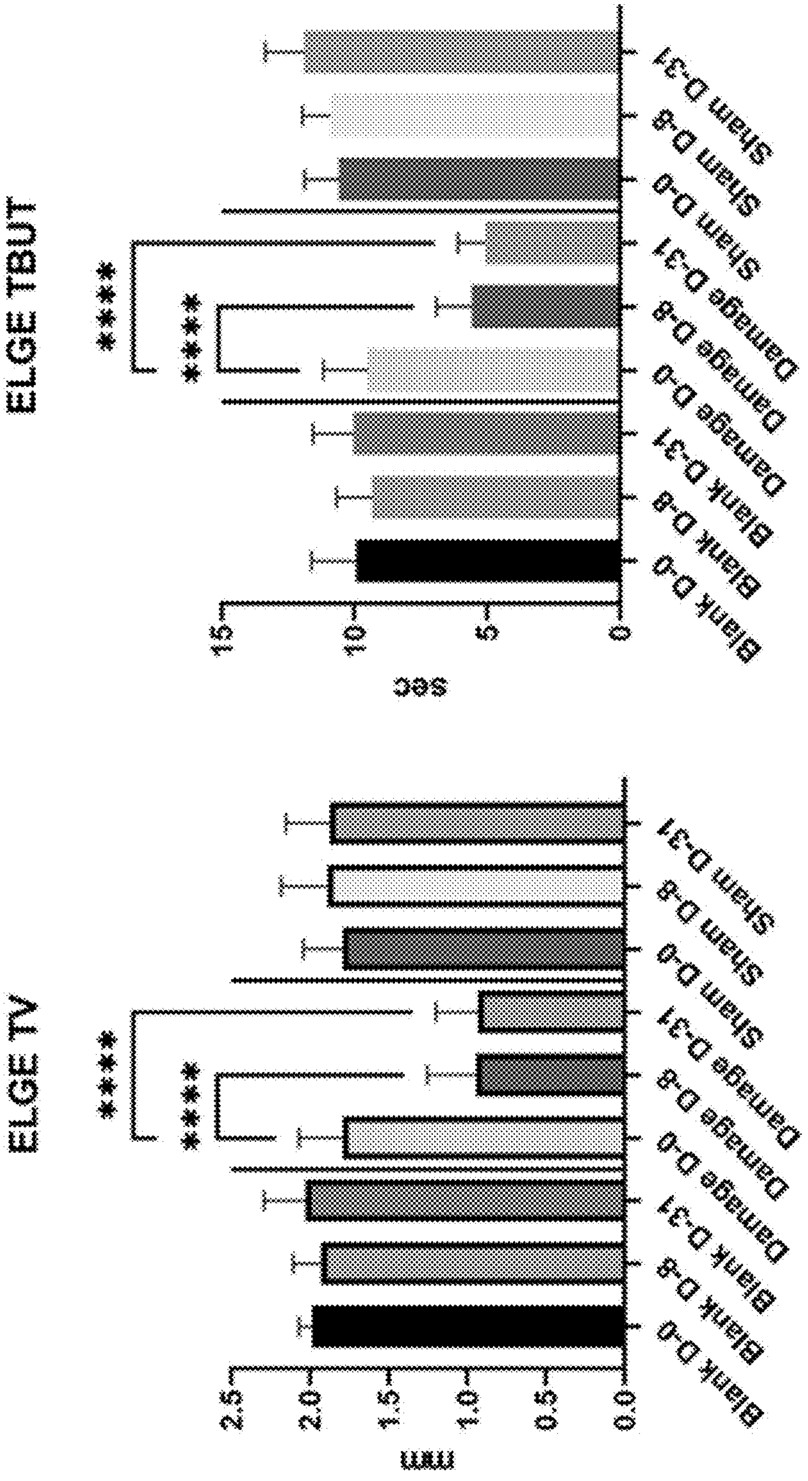
FIG. 7 depict tear volume (TV) and tear film break-up time (TBUT) for aqueous-deficient dry eye (ADDE) model FIG. 8 depict cornea lissamine green staining for aqueous-deficient dry eye (ADDE) model.

The results of aqueous-deficient dry eye (ADDE) model showed that after 0, 8, and 31 days of injury, tear volume measurement and tear film break-up time tests were conducted. In terms of tear volume changes, the injury group showed a significant decrease in tear volume after injury induction, while the control group and sham surgery group showed no significant changes. Similarly, the tear film break-up time also exhibited the same pattern. This injury model demonstrates the successful induction of our experimental injury model. (FIG. 7).

Figure 11:
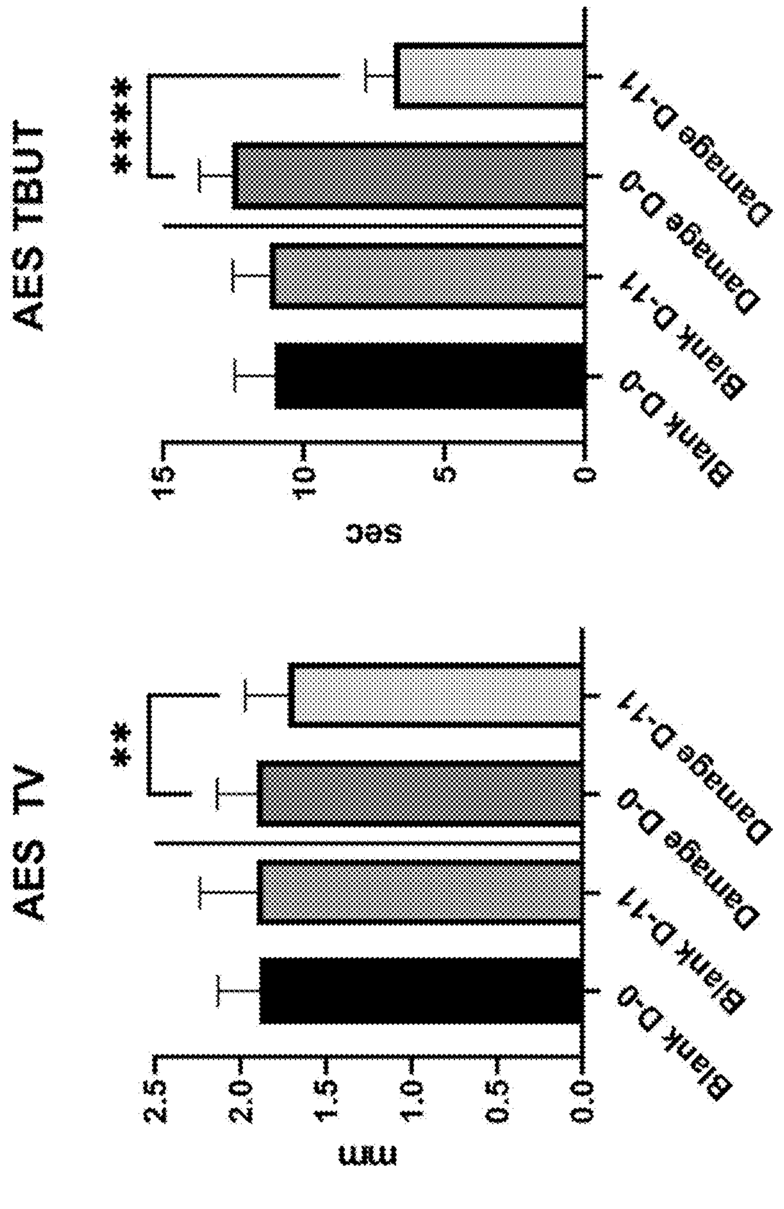
FIG. 11 depict tear volume (TV) and tear film break-up time (TBUT) for evaporative dry eye (EDE) model.

The results of evaporative dry eye (EDE) model showed that tear volume measurement and tear film break-up time tests were conducted before and after 10 days of injury induction. In terms of tear volume changes, the injury group showed a significant decrease in tear volume after injury induction, while the control group showed no significant changes. Similarly, the tear film break-up time also exhibited the same pattern. This injury model demonstrates the successful induction of our experimental injury model. (FIG. 11).

Figure 15:
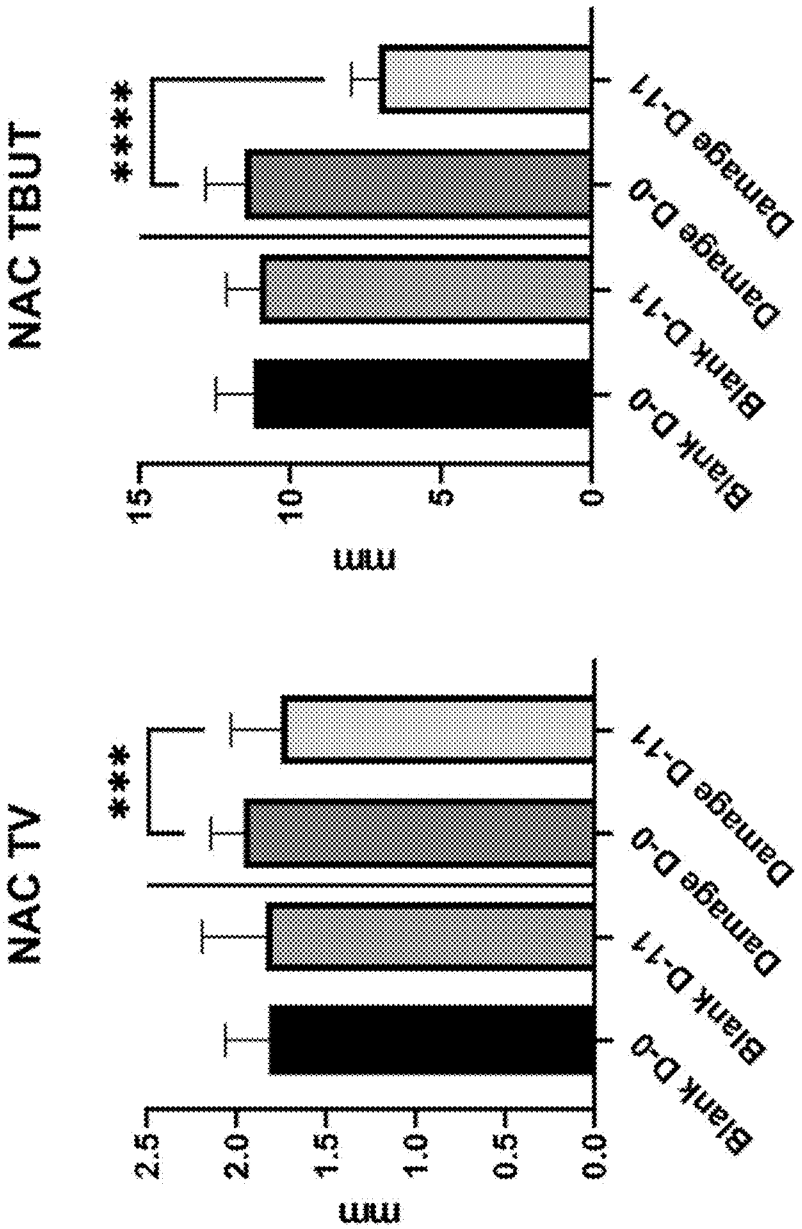
FIG. 15 depict tear volume (TV) and tear film break-up time (TBUT) for mucin-deficient dry eye model.

The results of mucin-deficient dry eye model showed that tear volume measurements and tear film break-up time tests were performed before and after a 10-day period of injury induction. In terms of tear volume changes, the injury group exhibited a significant decrease in tear volume following injury induction, while the control group showed no significant changes. Similarly, the tear film break-up time demonstrated a similar pattern. This injury model serves as evidence of the successful induction of our experimental injury model. (FIG. 15)

Example 4

Grading of Cornea Staining for OSD Model

The damages of cornea surface were examined based on the extent of lissamine green stain, according to a previous publication. Each cornea was stained with 3 μL of 1% lissamine green (Sigma-Aldrich, St. Louis, MO). Images of cornea staining were taken under a dissecting microscope (SMZ 645: Nikon, Tokyo, Japan) and graded according to the following criteria. The cornea is divided into four quadrants. In each quadrant, the staining was differentiated into 4 levels: absent (grade 0), light (grade 1), moderate (grade 2), and severe (grade 3). The total grades of the four quadrants were summed for each eye.

Figure 3:
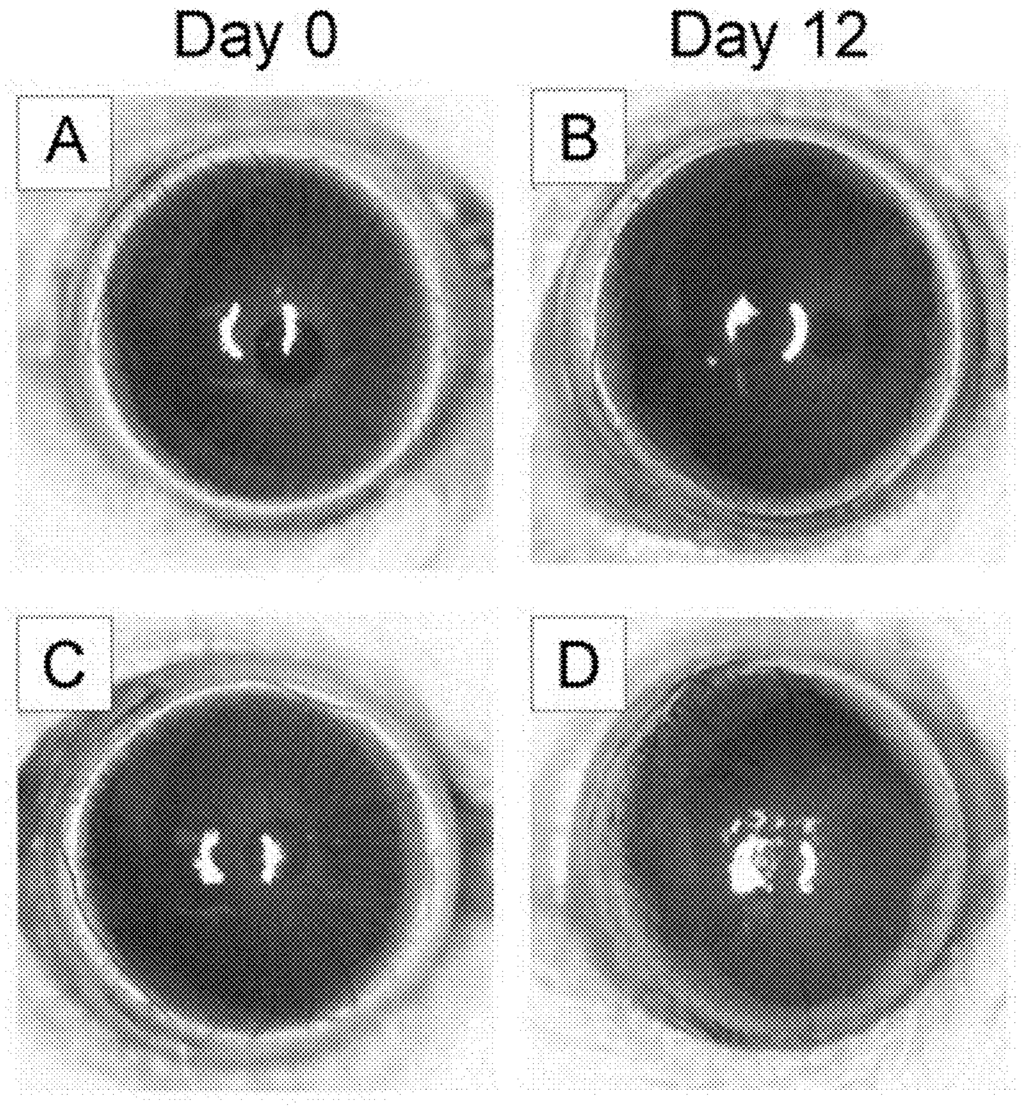
FIG. 3A-3D depict that representative photos of cornea lissamine green staining on days 0 and 12.

The results of photokeratitis model showed that severe opacity was found in the UVB-damaged cornea on day 11, after 10 days of UVB exposure (compare FIGS. 3B and 3D). The grade of cornea staining was significantly higher in the damage group compared with that of the blank group (Table 1)

TABLE 1

The average of cornea staining grades on days 0 and 12, with (damage) and without (blank) UVB exposure.

| Group | Day 0 | Day 12 |
|---|---|---|
| Blank | 1.92 (0.19) | 1.83 (0.21) |
| Damage | 1.83 (0.27) | 7.58 (0.58)**** |

****p < 0.0001, by Mann-Whitney U test;
n = 12 for both the blank and the damage groups of photokeratitis model.

Figure 8:
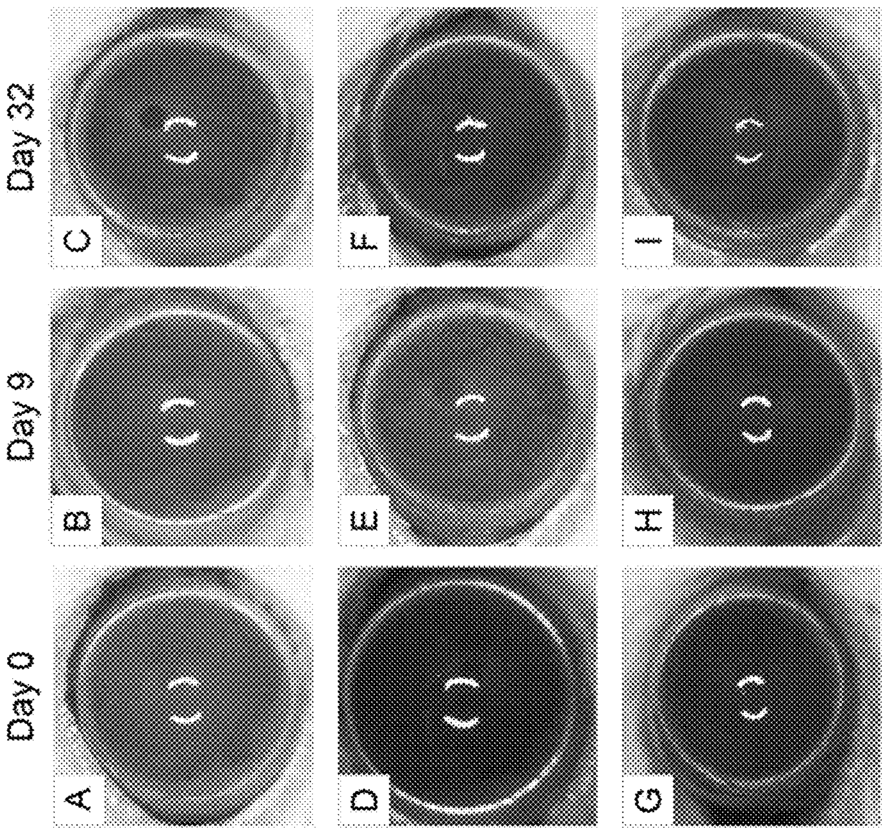
Figure 9:
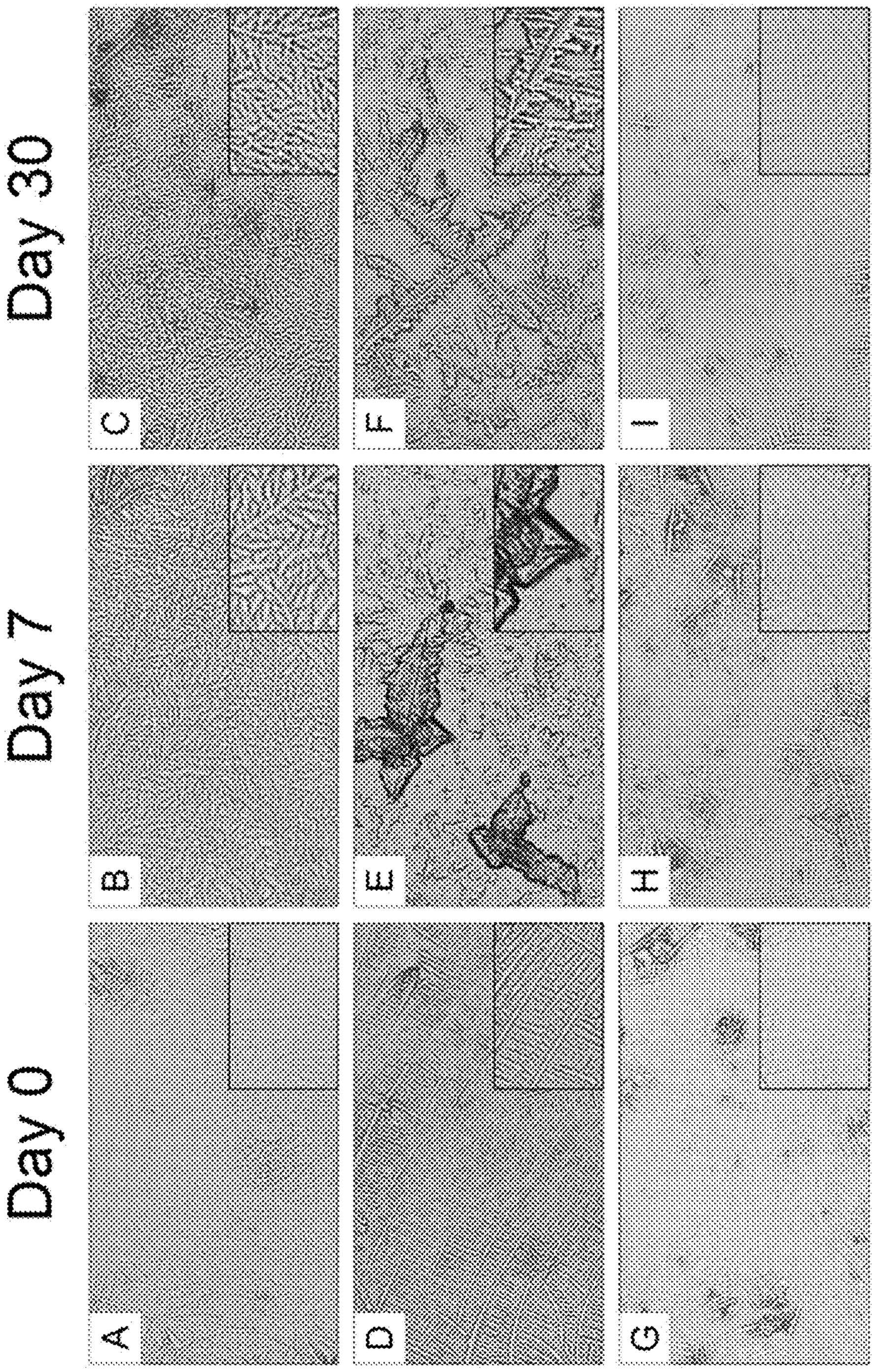

The results of aqueous-deficient dry eye (ADDE) model showed that following injury induction, the corneas of mice in the injury group exhibited significant pathological changes, characterized by an increase in the area of dye staining on the ocular surface. (FIG. 8) This was accompanied by a significant increase in the grading score. In contrast, the corneas of the control group and sham surgery group showed no pathological changes, and there were no significant variations observed in the grading score (Table 2).

TABLE 2

The average of cornea staining grades on days 0, 9 and 32 of aqueous-deficient dry eye (ADDE) model.

| Group | Day 0 | Day 9 | Day 32 |
|---|---|---|---|
| Blank | 1.67(0.26) | 1.42(0.23) | 0.83(0.27) |
| Damage | 2.17(0.24) | 6.5(0.58)**** | 6(0.51)*** |
| Sham | 1(0.25) | 0.5(0.23) | 0.5(0.19) |

Figure 12:
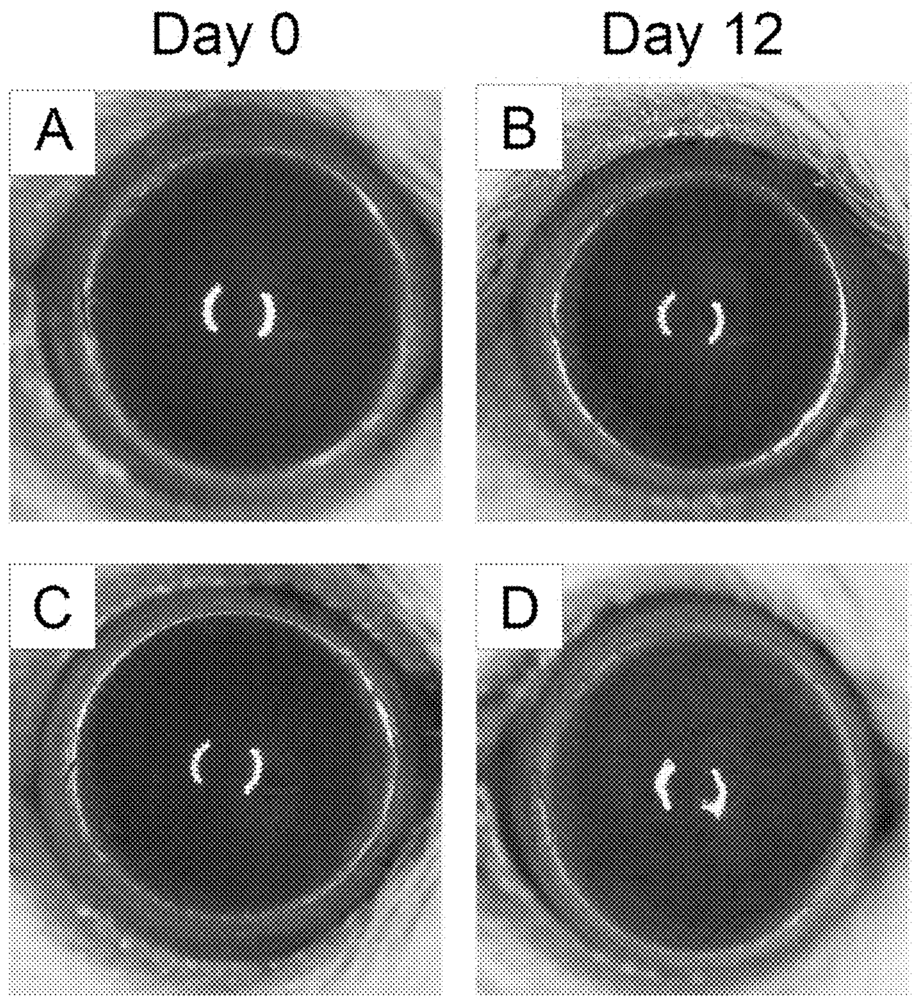
FIG. 12 depict cornea lissamine green staining for evaporative dry eye (EDE) model.
Figure 13:
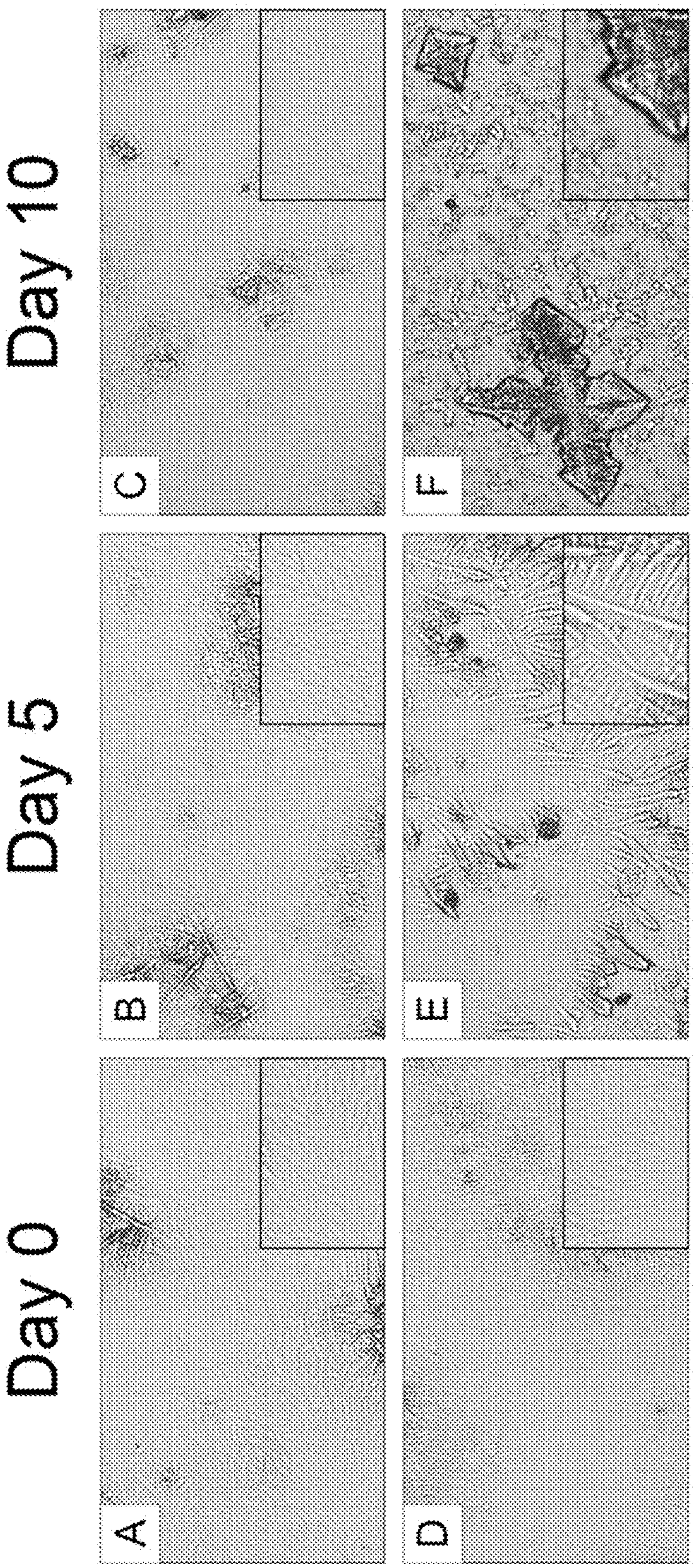

The results of evaporative dry eye (EDE) model showed that following injury induction, the corneas of mice in the injury group exhibited significant pathological changes, resulting in a significant increase in the grading score (FIG. 12). In contrast, the corneas of the control group showed no pathological changes, and there were no significant variations observed in the grading score (Table 3).

TABLE 3

The average of cornea staining grades on days 0 and 12 of evaporative dry eye (EDE) model.

| Group | Day 0 | Day 12 |
|---|---|---|
| Blank | 0.92(0.36) | 1.67(0.36) |
| Damage | 1(0.17) | 4.58 (0.38)**** |

Figure 16:
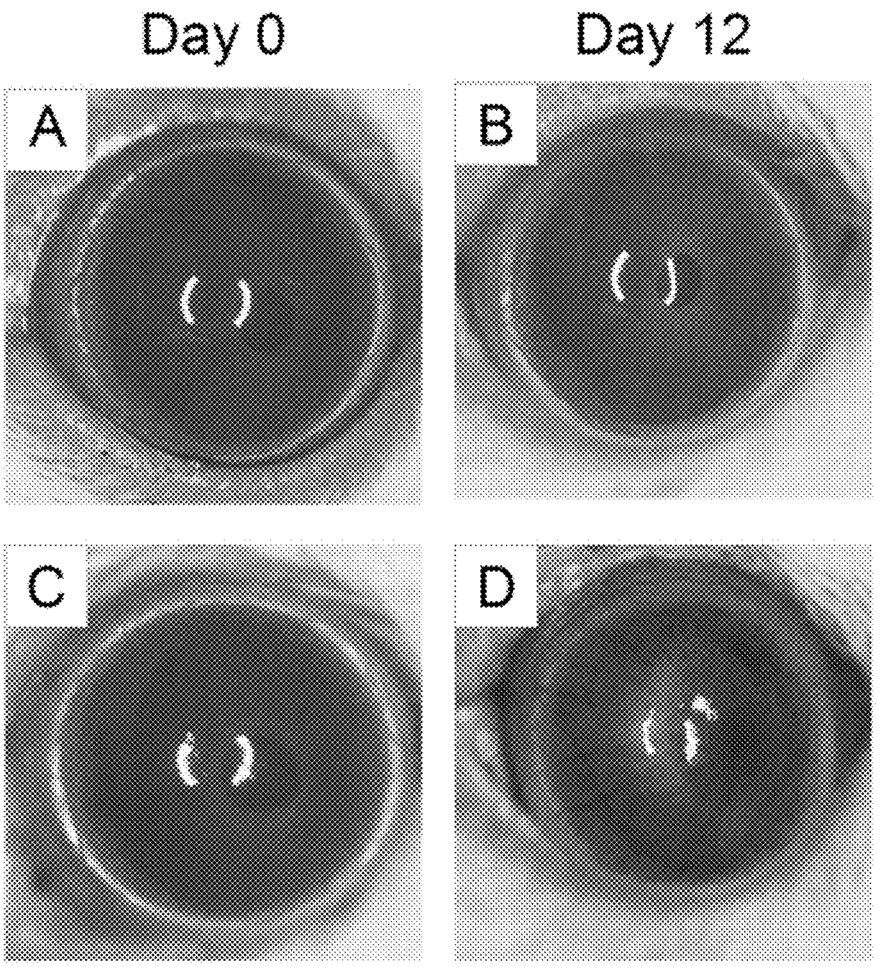
FIG. 16 depict cornea lissamine green staining for mucin-deficient dry eye model.
Figure 17:
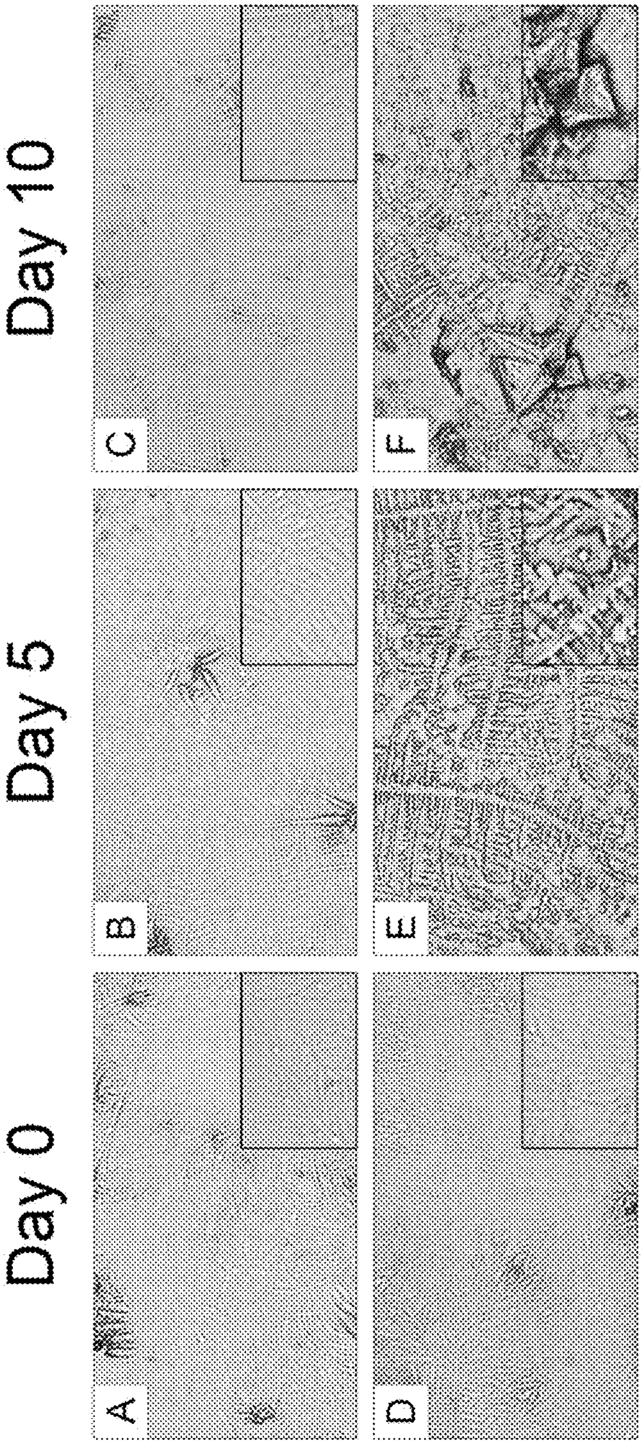
FIG. 17A-17F depict Tear Ferning patterns (TF) for mucin-deficient dry eye model.

The results of mucin-deficient dry eye model showed that following injury induction, the corneas of mice in the injury group exhibited significant pathological changes, resulting in a significant increase in the grading score. In contrast, the corneas of the control group showed no pathological changes, and there were no significant variations observed in the grading score (FIG. 16) (Table 4). In the experimental group, it was observed that the administration of NAC eye drops led to the formation of a circular white haze on the ocular surface of mice.

TABLE 4

The average of cornea staining grades on days 0 and 12 of mucin-deficient dry eye model.

| Group | Day 0 | Day 12 |
|---|---|---|
| Blank | 1.67(0.14) | 1.67(0.14) |
| Damage | 1(0.25) | 6.75 (0.45)**** |

Example 5

TF Procedures

Tear samples were collected with wash solution containing 0.4% NaCl with the pH value maintained at 7.5±0.2. After anesthesia, a drop of 2 μL wash solution was added onto the ocular surface with a micropipette set perpendicular to the cornea. The drop was pipetted thirty to forty times to wash thoroughly the ocular surface, avoiding loss of the solution and damage to the ocular surface. All TF tests were performed immediately after sample collection. For each test, 1.5 μL sample was placed onto a glass slide and air-dried in an oven (LE-509RH: Yih Der, Taiwan) for 10 minutes at 24±2° C. and relative humidity (rH) 46±3%. Each TF formation was photographed under a light microscope (DM500: Leica, Wetzlar, Germany) by 40× and 100× magnification.

Example 6

TF Grading

The patterns of TF images were graded in accordance with the Masmali and the SK gradings. The SK grading is a new set of criteria modified from the Masmali method to describe TF ranging from 0 to 4 by 0.5 incremental scales.

The SK gradings were based on TF crystal patterns and non-crystal spaces as demonstrated by the area of orange color on the lower left box in each magnified photo in FIG. 1A-1I (as demonstrated by photokeratitis model).

Generally; more and wider spaces were observed as the grades getting higher. Grade 0 in FIG. 1A was designated with the presence of dense radiating snowflake patterns (as indicated by black arrow in FIG. 1A) while their surrounding details too subtle to be discerned. Grade 0.5 in FIG. 1B exhibited complex patterns and had more evident non-crystal spaces than grade 0. Also, grade 0.5 had fine trunk crystals (indicated by black triangles). Grade 1 in FIG. 1C mainly formed fine branching patterns with even more non-crystal spaces. Compared with grade 0.5, the trunk crystals were coarser (indicated by blue triangles). Grade 1.5 in FIG. 1D had even coarser trunk crystals compared with grade 1 (indicated by yellow triangles). The fine branches appeared more irregular than those of grade 1. For grade 2 in FIG. 1E, most of the TF crystals were intersected at right angles (indicated by right angle marks in dark-gray) and the gaps between neighboring branches became wider. For grade 2.5 in FIG. 1F, the intersected TF crystals became broken and more non crystal spaces were identified. Grade 3 in FIG. 1G exhibited large unbranched crystals in a cross shape (indicated by black arrow in FIG. 1G) and much more non-crystal spaces were observed. Grade 3.5 in FIG. 1H contained crystals with shorter arms and were even square-like in shape (indicated by black arrow in FIG. 1H). Grade 4 in FIG. 1I showed much less presentation of crystals, almost close to none, and the largest non-crystal area.

Example 7

TF Patterns for OSD Model

Figure 4:
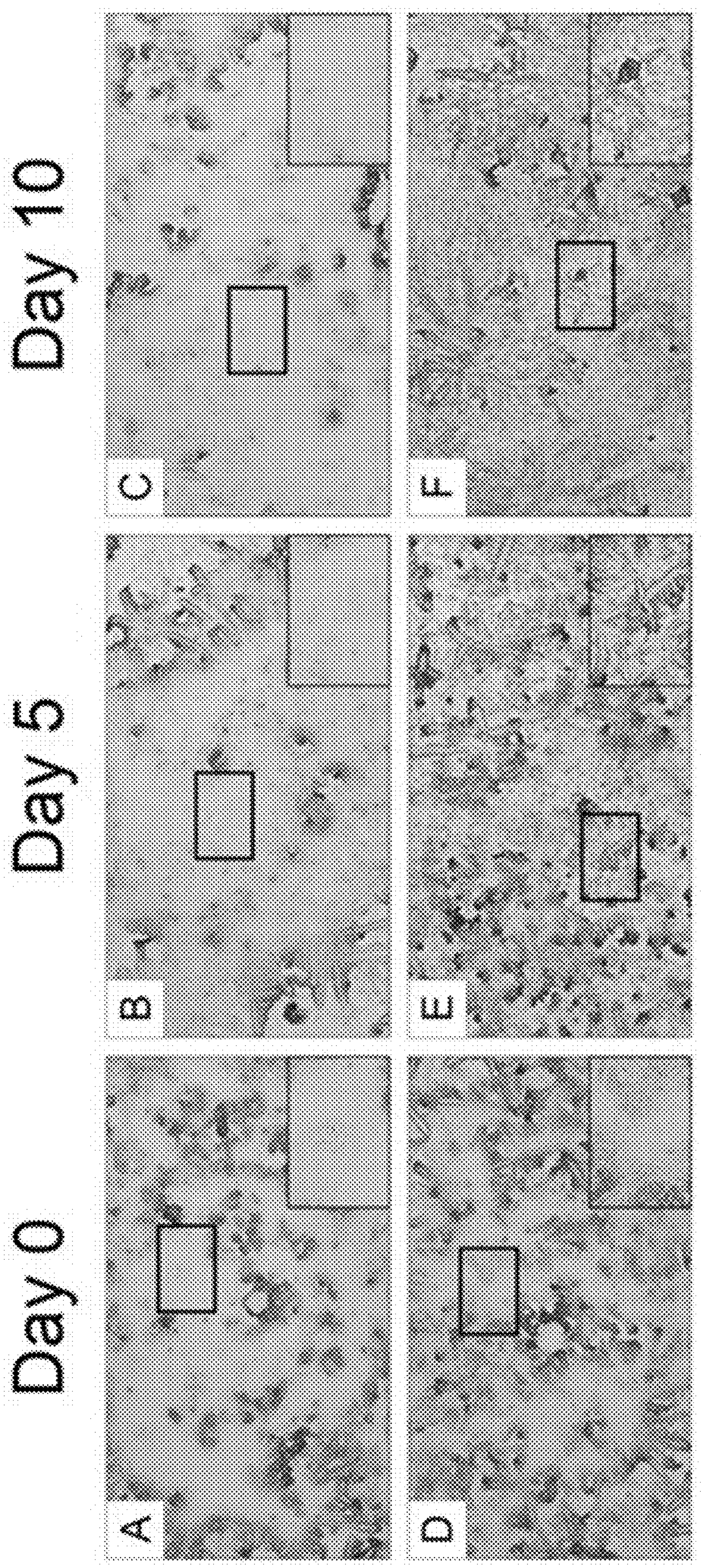
FIG. 4 depict that TF patterns on days 0 (FIG. 4A, 4D), 5 (FIG. 4B, 4E), 10 (FIG. 4C, 4F), respectively. The red boxed areas are magnified and presented on the lower right corner of each photo to show the specific characteristics of TF patterns of photokeratitis model. All original photos were taken at 100× magnification.

The TF results of the damage and the blank groups on days 0, 5, and 10 were compared. The results of photokeratitis model showed that on day 5 after UVB exposure, the TF pattern showed more coarse trunks and non-crystal spaces in the damage group (FIG. 4E) compared to that of the blank group (FIG. 4A, B, C) and that before UVB damage on day 0 (FIG. 4D). On day 10 after UVB exposure, the TF pattern was significantly scattered and with short crystal formation that was square-like in shape (FIG. 4F). Moreover, even more non-crystal spaces could be observed in the TF pattern after 10 days of UVB exposure. However, the TF test results from the blank group on days 0, 5, and 10 showed dense snowflake patterns without non-crystal spaces (FIG. 4A, 4B, 4C). No difference was observed in the blank group on different days. A trend of less TF formation was observed after UVB exposure (compare FIG. 4D with FIG. 4E and FIG. 4F).

In other words, the status of photokeratitis may also alter tear components and functionality, leading to changes in TF patterns, which has been demonstrated in present embodiment.

The results of aqueous-deficient dry eye (ADDE) model showed that in the injury group, it was observed that tear crystallization underwent changes from pre-injury to the onset of injury. As time progressed, the tear crystallization became increasingly fragmented. However, no significant changes in tear crystallization were observed in the control group and sham surgery group (FIG. 9A-9I).

The results of evaporative dry eye (EDE) model showed that in the injury group, it was observed that tear crystallization underwent changes from pre-injury to the onset of injury. As time progressed, the tear crystallization became increasingly fragmented and large cross-shaped crystals emerged. In contrast, the control group showed no significant changes in tear crystallization (FIG. 13A-13F).

Example 8

Relatively Early TF Detection by SK Grading

Figure 5:
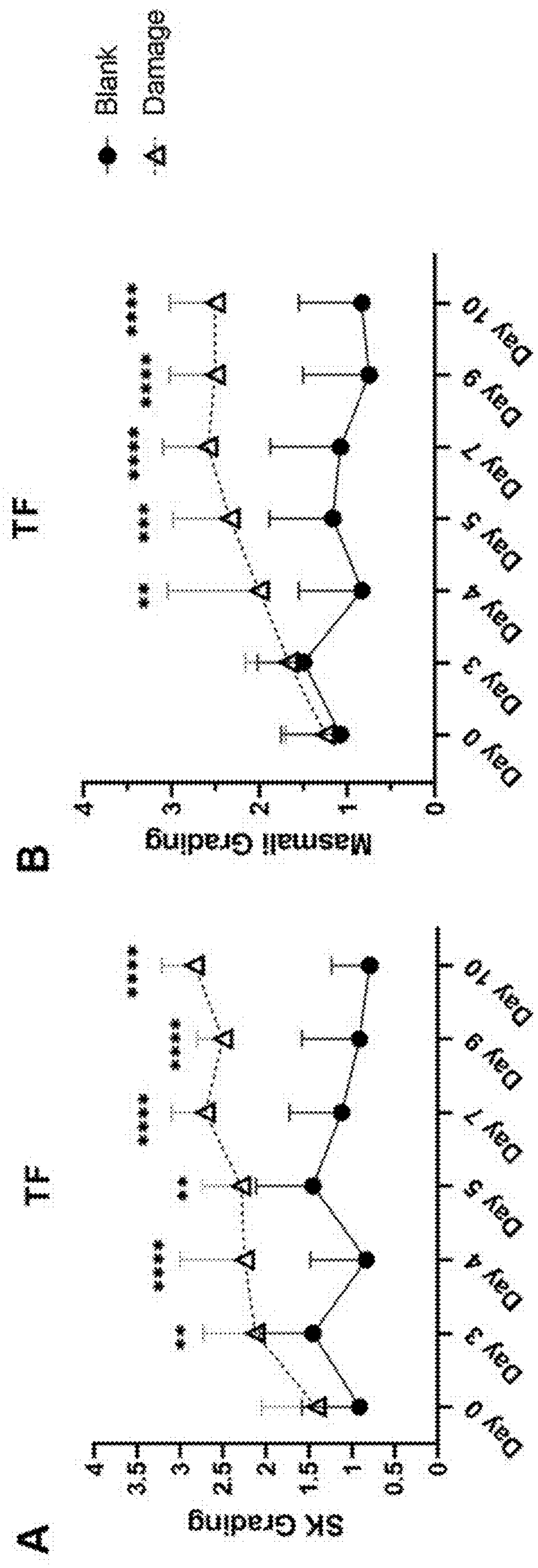
FIG. 5A-5B depict that Tear ferning (TF) gradings by the Sophie-Kevin (SK) (FIG. 5A) and the Masmali grading (FIG. 5B) criteria. The SK grading displayed significant difference between the blank and the damage groups on day 3, one day earlier than the Masmali grading.  $p<0.01$: * $p<0.001$: **** $p<0.0001$; n=12 for both the blank and the damage groups of photokeratitis model: all statistics were performed by Mann-Whitney U test.

TF grades using both grading criteria were increased along with the days of experiment except for the blank group. The results of photokeratitis model showed that the to determine which set of TF grading criteria is more suitable for early photokeratitis diagnosis in the mouse model, the SK and the Masmali grading criteria were compared. Using the SK grading criteria, the TF results increased from an average grade of 1.42 (SEM±0.18) before UVB exposure to 2.13 (SEM±0.18) after 3 days of UVB exposure. After 10 days, the average TF grade increased to 2.83 (SEM±0.11). A significant difference in TF grades was found between the blank and the damage groups as early as on day 3 (p<0.01) (Table 5). In contrast, by using the Masmali grading criteria, the average of TF grades was only slightly increased from 1.25 (SEM±0.13) to 1.67 (SEM±0.14) after 3 days of UVB exposure. (FIGS. 5A and 5B) The TF tests revealed no significant differences between the blank and the damage groups on day 3 by using the Masmali criteria.

TABLE 5

The average tear ferning (TF) grades by the Sophie-Kevin (SK) and the Masmali grading criteria on days 0, 3, 4, 5, 7, 9, 10, with (damage) or without (blank) UVB exposure.

| | Group | Day 0 | Day 3 | Day 4 | Day 5 | Day 7 | Day 9 | Day 10 |
|---|---|---|---|---|---|---|---|---|
| SK Grading | Blank | 0.92 (0.19) | 1.46 (0.18) | 0.83 (0.19) | 1.46 (0.19) | 1.13 (0.18) | 0.92 (0.19) | 0.79 (0.13) |
| | Damage | 1.42 (0.18) | 2.13 (0.18)** | 2.25 (0.22)**** | 2.29 (0.13)** | 2.71 (0.11)**** | 2.5 (0.09)**** | 2.83 (0.11)**** |
| Masmali Grading | Blank | 1.08 (0.19) | 1.50 (0.15) | 0.83 (0.21) | 1.17 (0.21) | 1.05 (0.23) | 0.75 (0.22) | 0.83 (0.21) |
| | Damage | 1.25 (0.13) | 1.57 (0.14) | 2 (0.30)** | 2.33 (0.19)*** | 2.58 (0.15)**** | 2.5 (0.15)**** | 2.5 (0.15)**** |

**p < 0.01,
***p < 0.001,
****p < 0.0001;
n = 12 for both the blank and the damage groups; all statistics were performed by Mann-Whitney U test.

Figure 10:
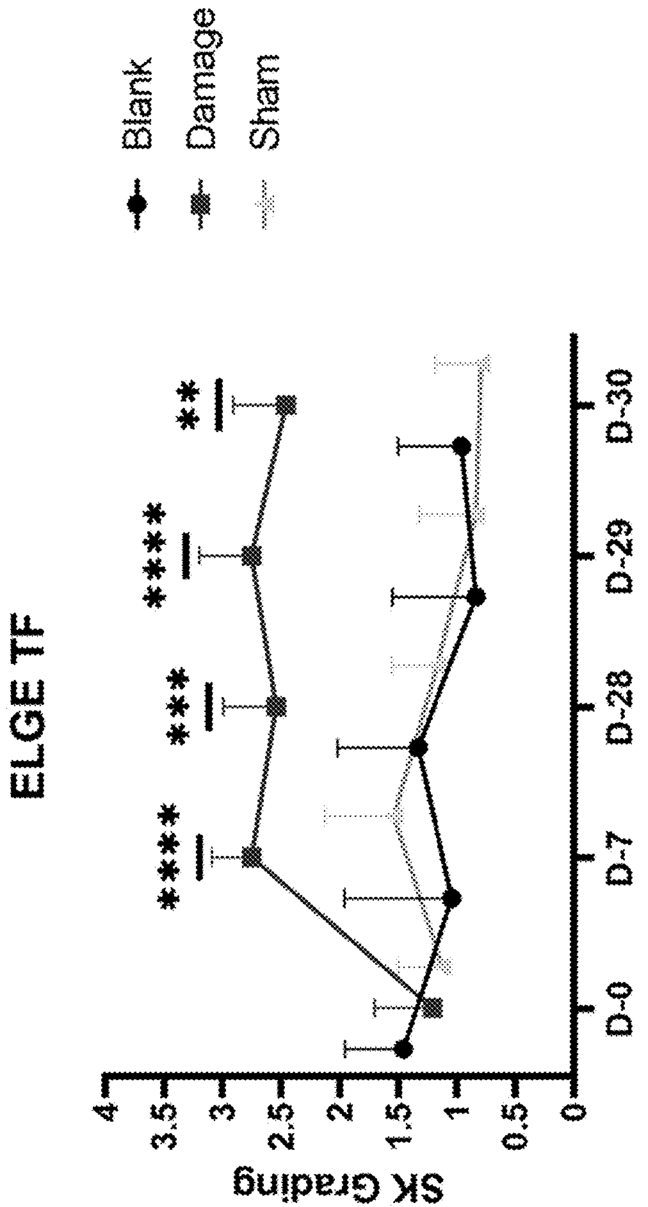
FIG. 10 depicts that Tear ferning (TF) gradings of aqueous-deficient dry eye (ADDE) model by the Sophie-Kevin (SK) criteria.

Using the SK grading criteria, statistical analysis revealed a significant difference in tear crystallization levels between the injury group after the seventh day and before the injury in aqueous-deficient dry eye (ADDE) model. However, no significant differences were observed in tear crystallization levels between the control group and sham surgery group (FIG. 10).

Figure 14:
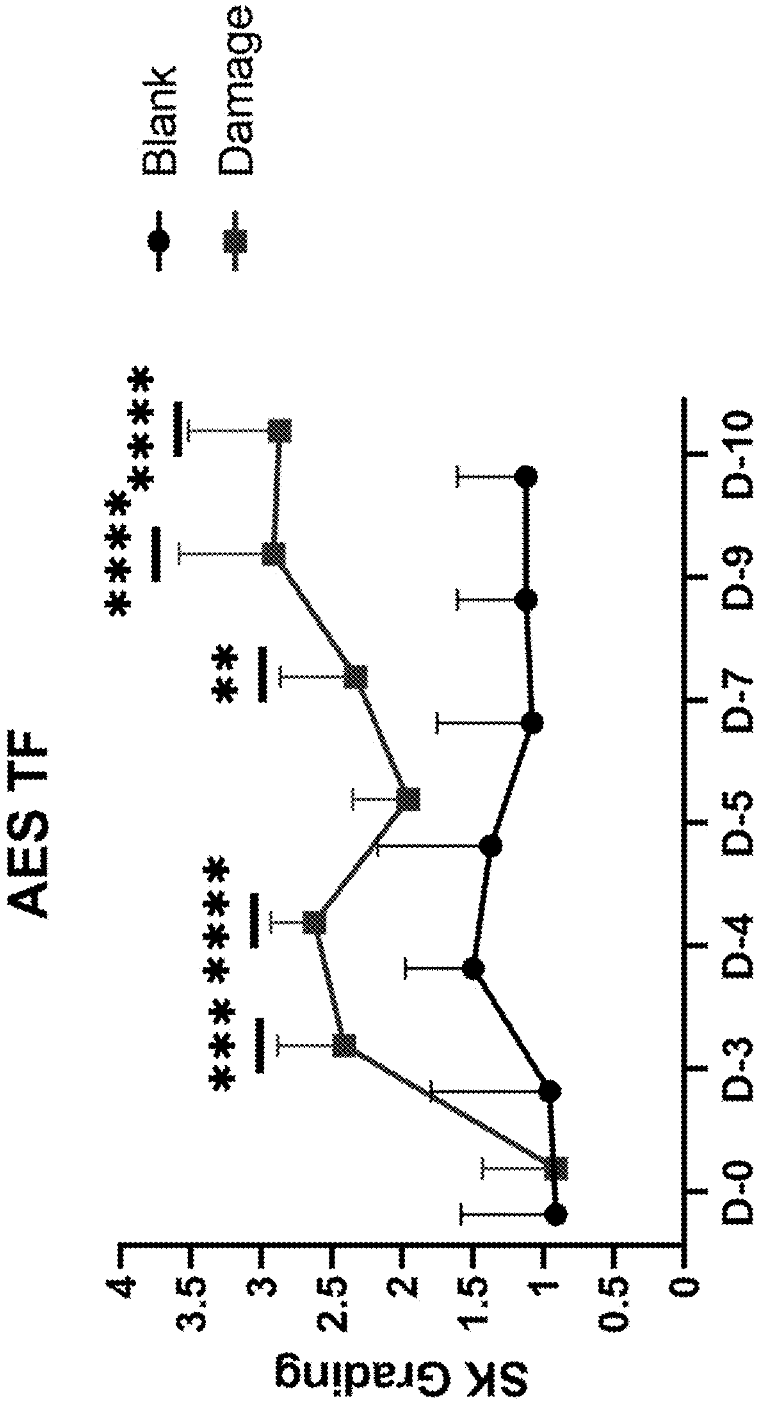
FIG. 14 depict that Tear ferning (TF) gradings of evaporative dry eye (EDE) model by the Sophie-Kevin (SK) criteria.

Another, statistical analysis revealed a significant difference in tear crystallization levels between the injury group after the third day and before the injury in evaporative dry eye (EDE) model (FIG. 14).

Figure 18:
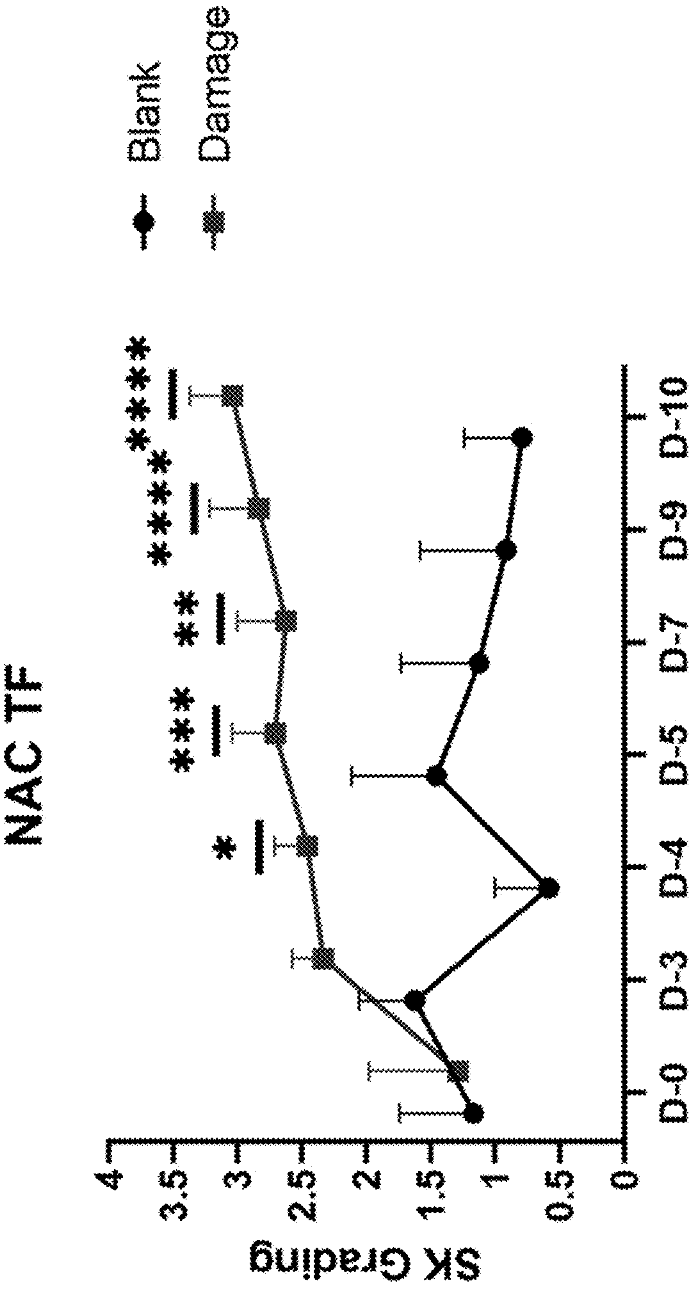
FIG. 18 depict that Tear ferning (TF) gradings of mucin-deficient dry eye model by the Sophie-Kevin (SK) criteria.

The other, statistical analysis revealed a significant difference in tear crystallization levels between the injury group after the fourth day and before the injury in mucin-deficient dry eye model (FIG. 18).

Example 9

Correlation Between TF Test and Other Ocular Surface Indicators

Since the SK grading was found to be more sensitive for early diagnosis, the test results were further correlated with other ocular surface indicators, including TV, TBUT, and cornea staining.

Figure 6:
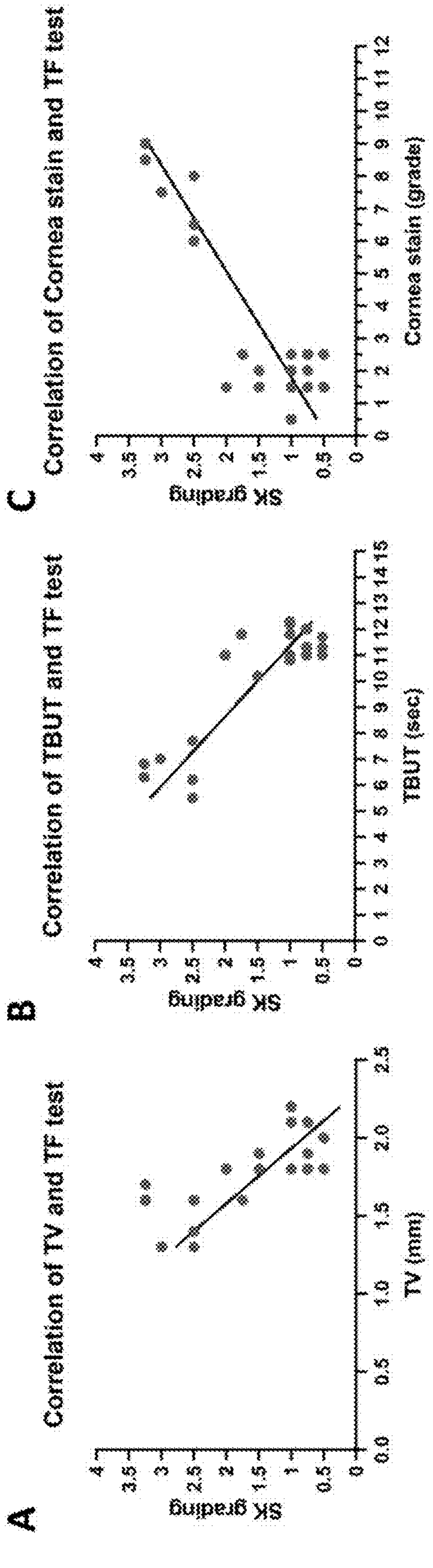
FIG. 6A-6B depict that the correlation of tear ferning (TF) results by the Sophie-Kevin (SK) grading criteria with tear volume (TV), tear film break-up time (TBUT), and cornea staining. mm, millimeter. sec, second.
(FIG. 6C): $r=0.887$, $p<0.0001$: n=12 for both the blank and the damage groups of photokeratitis model: all the statistics were performed by Pearson r test.

The results of photokeratitis model showed that in all the study groups, the negative correlation between the TF test and the TV test was strong (r=−0.702, p=0.0001) (FIG. 6A). A very strong negative correlation (r=−0.878, p<0.0001) between the TF test and the TBUT was also observed (FIG. 6B). Furthermore, a very strong positive correlation (r=0.887, p<0.0001) between the TF test and the cornea staining was also found (FIG. 6C).

In this invention, the TF test was investigated for its capacity to distinguish between normal and early photokeratitis status in a mouse UVB-induced model. With photokeratitis, although both the Masmali and the SK criteria could distinguish the damage from the blank groups after 4 days, the SK criteria could discern the damage group on day 3. This capacity of earlier detection would render the SK criteria more helpful if the TF test is used in the clinical settings. This advantage of the SK criteria is likely due to that the subtler changes can be reflected To further verify the TF test as a reliable method for early photokeratitis diagnosis, we correlated the TF results with other commonly used clinical ocular surface parameters. The TF test showed strong correlations with TV, TBUT, and cornea staining, indicating that the TF test may provide a general view of all the three indicators under the photokeratitis status. Besides, the TF test correlation with TBUT was stronger than with TV, suggesting that the TF test can reflect more about tear quality than quantity. However, to bring the TF test into clinical settings, human clinical trials are mandatory to confirm its applicability as an earlier indicator for OSD.

In conclusion, the results of the present study have proven the capacity of the TF test for early diagnosis of OSD, particularly by using the SK grading criteria. Furthermore, since the TF test can generally reflect the results of TV, TBUT, and cornea staining, it may be used as a primary test before the other three measurement.

Example 10

Different Wash Solution Concentrations Affected Both TF Patterns and Gradings of Different Strain Mice Animals 20 8-week-old female Institute of Cancer Research (ICR) mice were purchased from BioLASCO Taiwan Co., Ltd (Taipei, Taiwan) and 20 8-week-old C57BL/6J mice were purchased from National Laboratory Animal Center (Taipei, Taiwan). The mice were examined and confirmed to be without clinical or ophthalmic diseases.

Preparation of Wash Solutions

The wash solutions were prepared at various concentrations (0.9%, 0.74%, 0.4% NaCl) at a stable pH value at 7.5±0.2. Initially, non-pH-stabilized 0.9% NaCl was used as wash solution. However, this wash solution irritated the eyes and caused responsive tear secretion as the pH value was at around 5.5 and would decline gradually in atmosphere. To minimize the non-physiological impact, we stabilized the pH value at 7.5±0.2, by adding 0.146 g $Na_2HPO_4$ and 0.0222 g $KH_2PO_4$ in 100 ml 0.9% NaCl stock solution, and used it to prepare wash solutions of various concentrations. Either the non-pH-stabilized (pH 5.5) or the pH-stabilized (pH 7.5) 0.9% NaCl were used to study the effects of pH value, wash solution concentration, and mouse strain on the TF results.

Tear Sample Collection

2 μL of wash solution was dropped on the cornea with a micropipette to wash the ocular surface. The wash was performed with repetitive pipetting for thirty to forty times, followed by sample collection from the conjunctival sac. All tear samples were collected in microtubes and immediately applied for the TF test without refrigeration. For the pH-stabilized wash solution tests, a total of 12 eyes were applied for tear collection. Each eye was washed with wash solution 3 times for triple repeat assessments (n=36). Each wash was performed at intervals more than 24 hr. For the effects of different NaCl concentrations, a total of 16 eyes were applied for tear collection (n=48).

Figure 19:
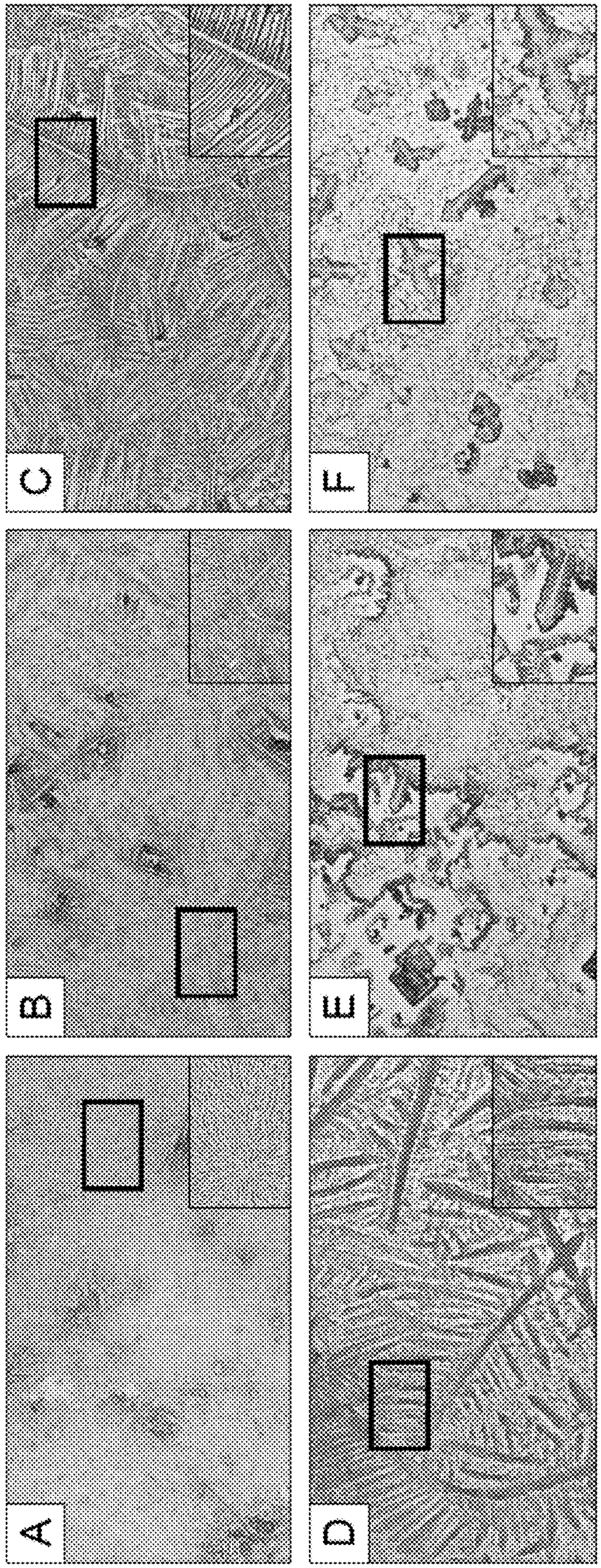
FIG. 19A-19D depict that the tear ferning patterns by using non-pH-stabilized 0.9% NaCl (pH at 5.5) as wash solution in ICR mice (FIG. 19A-19C) and C57BL/6J mice (FIG. 19D-19F) (100×). The inlets on lower right corner of FIG. 19A-19F represented the magnified TF patterns within each red box.

Differential TF Between ICR Mice and C57BL/6J Mice by Using 0.9% NaCl as Wash Solution The ICR mouse TF displayed fine branching or fern-leaf patterns that could be visible after further magnification (FIG. 19A-19C). In contrast, the C57BL/6J mouse TF consisted of scattered and amorphous crystals (FIG. 19D-19F). In most cases, the C57BL/6J mouse TF crystal patterns were restricted and the inter-crystal spaces were observed.

Figure 20:
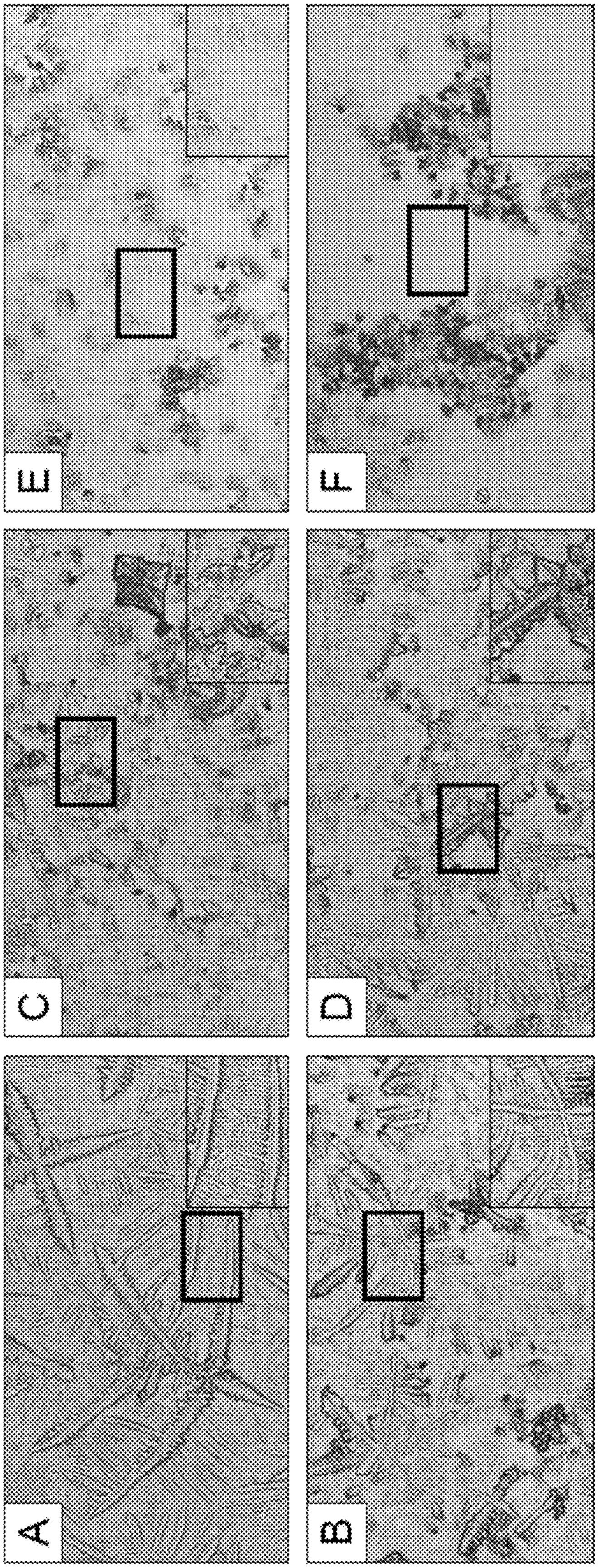
FIG. 20A-20F depict that the tear ferning patterns of C57BL/6J mice by using 0.9% NaCl (FIG. 20A-20B), 0.74% NaCl (FIG. 20C-20D), and 0.4% NaCl (FIG. 20E-20F). (100×). The inlets on lower right corner of FIG. 20A-20F represented the magnified TF patterns within each red box.

Wash Solution Concentrations Affected Both TF Patterns and Gradings of C57BL/6J Mice The results of 0.9% NaCl showed crystal branches with robust trunks and voids (FIGS. 20A and 20B). When the 0.74% NaCl was used, the TF crystal formation was shorter and less complete with more voids than the result of 0.9% NaCl (FIGS. 20C and 20D). Using 0.4% NaCl wash solution, TF formation exhibited snowflake or fine branching patterns with thinner trunks and fewer voids than the results of 0.9% NaCl (FIGS. 20E and 20F).

Figure 21:
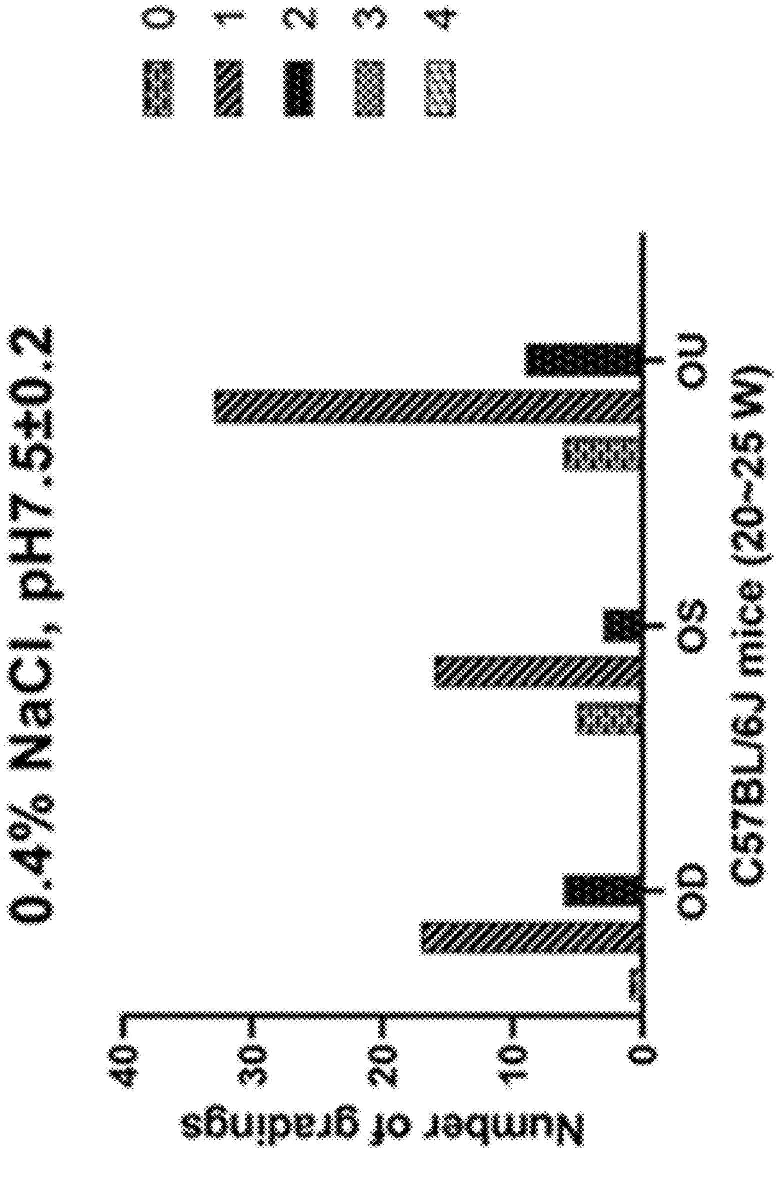
FIG. 21 depict that the histograms of tear ferning grade distribution of 20- to 25-week-old C57BL/6J mice by using pH-stabilized 0.4% NaCl as the wash solution, according to Masmali grading. * $p<0.05$, 0.4% group versus 0.74% group (grade 0 to grade 2).

For TF grading distribution, most gradings were at grade 1 (68.8%) by Masmali grading when using 0.4% NaCl (FIG. 21).

The SK Grading Reflected Normal TF Distribution and Subtle Disparity

Figure 22:
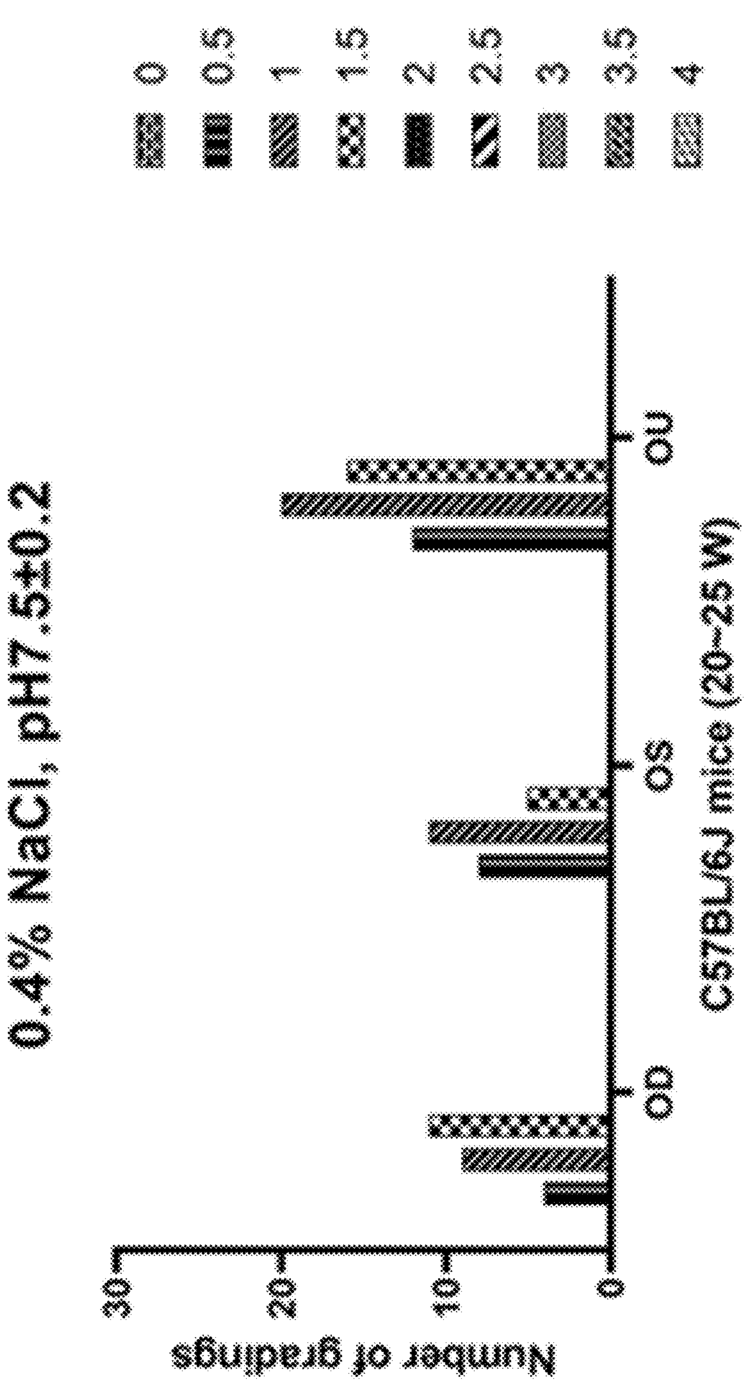
FIG. 22 depict that the histograms of tear ferning grade distribution of 20- to 25-week-old C57BL/6J mice by using pH-stabilized 0.4% NaCl as the wash solution, according to SK grading. * $p<0.05$, 0.4% group versus 0.9% group, 0.4% group versus 0.74% group (grade 0.5 to grade 1.5).

By using the SK grading, when using 0.4% NaCl wash solution, most TF formations were graded 1 (41.7%), with some results of grade 0.5 (25.0%) and 1.5 (33.3%) (FIG. 22).

Comparison Between the SK and the Masmali Gradings

Figure 23:
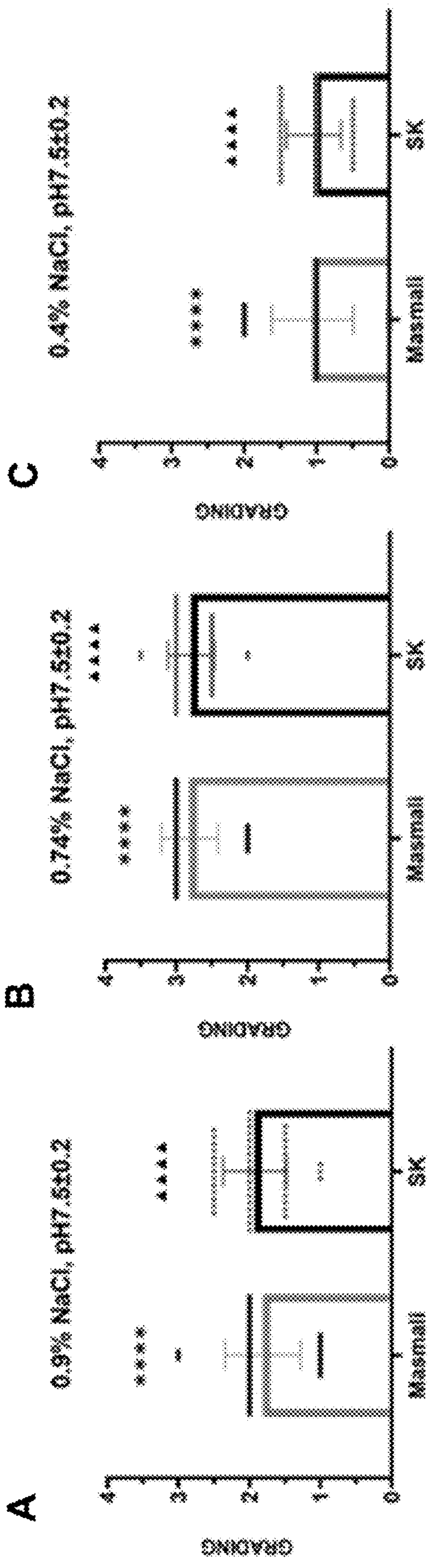
FIG. 23A-23C depict that the histograms with scatter plots of tear ferning grades from 20- to 25-week-old C57BL/6J mice by using pH-stabilized 0.9%, 0.74%, 0.4% NaCl wash solutions. The gray dots represent the TF gradings from three repetitive tests, according to Masmali and SK grading, respectively. **** $p<0.0001$, for any two out of the three groups compared with each other, according to Masmali grading. AAAA $p<0.0001$, for any two out of the three groups compared with each other, according to SK grading.

With 0.9% NaCl wash solution, the Masmali grading showed between 1 to 3, whereas the SK grading was between 1 to 2.5, mostly between 1.5 to 2.5 (FIG. 23A). With the 0.74% NaCl wash solution, the Masmali grading ranged from 2 to 3, while the SK grading showed a range mostly between 2.5 to 3 (FIG. 23B). When using 0.4% NaCl wash solution, the Masmali grading ranged from 0 to 2, while the SK grading results were between 0.5 to 1.5 (FIG. 23C). The use of 0.4% NaCl lead to the number of grades 0 to 2 or 0.5 to 1.5, which was significantly different to those with 0.74% NaCl (p<0.05), in both the Masmali and the SK gradings. When the results of 0.4% were compared with those of 0.9% NaCl, only the SK gradings showed significant difference (p<0.05), in contrast to the non-significant findings using the Masmali gradings (p=0.0984). Although the TF results with 0.4% NaCl, either the Masmali or the SK grading, were generally below grade 2, the SK grading provided more discernable disparity for TF patterns.

Common Applicability of 0.4% NaCl for Both ICR and C57BL/6J Mice

Figure 24:
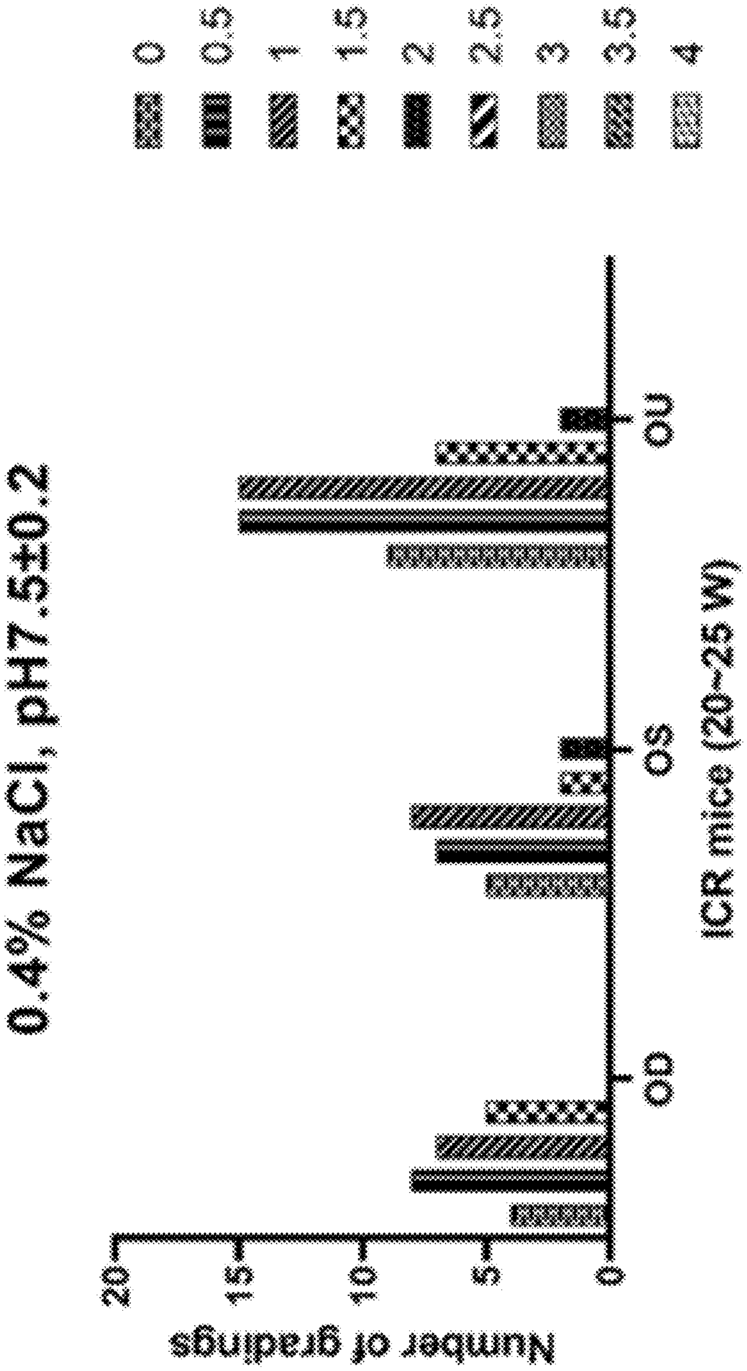
FIG. 24 depict that the histogram of tear ferning grade distribution of 20- to 25-week-old ICR mice by using pH-stabilized 0.4% NaCl wash solution, according to SK grading.
Figure 25A:
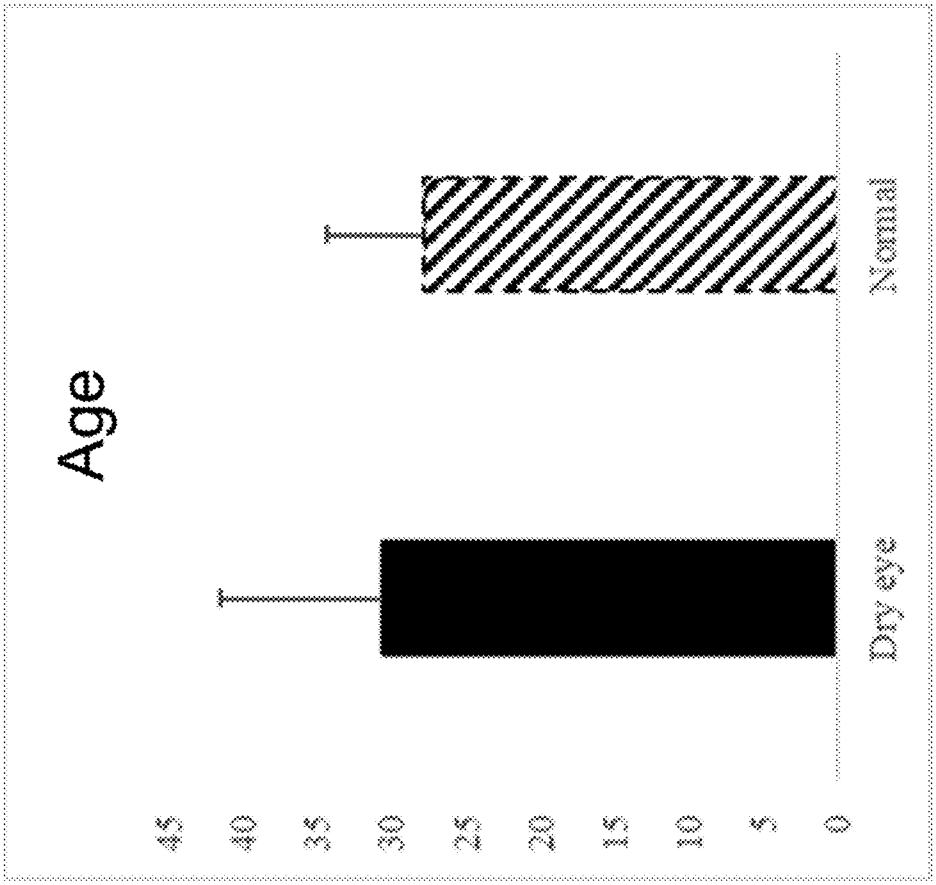
FIG. 25A-25F depict the histograms showing the data of the Table 6. * indicates significant differences ($p<0.05$).
Figure 25B:
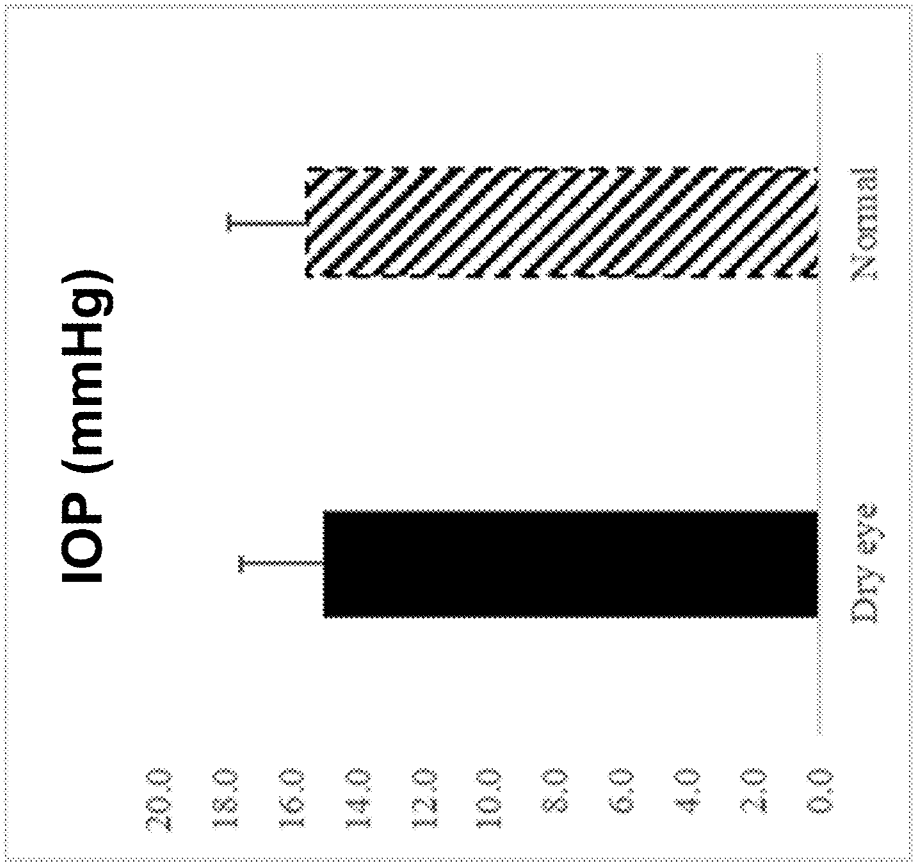
Figure 25C:
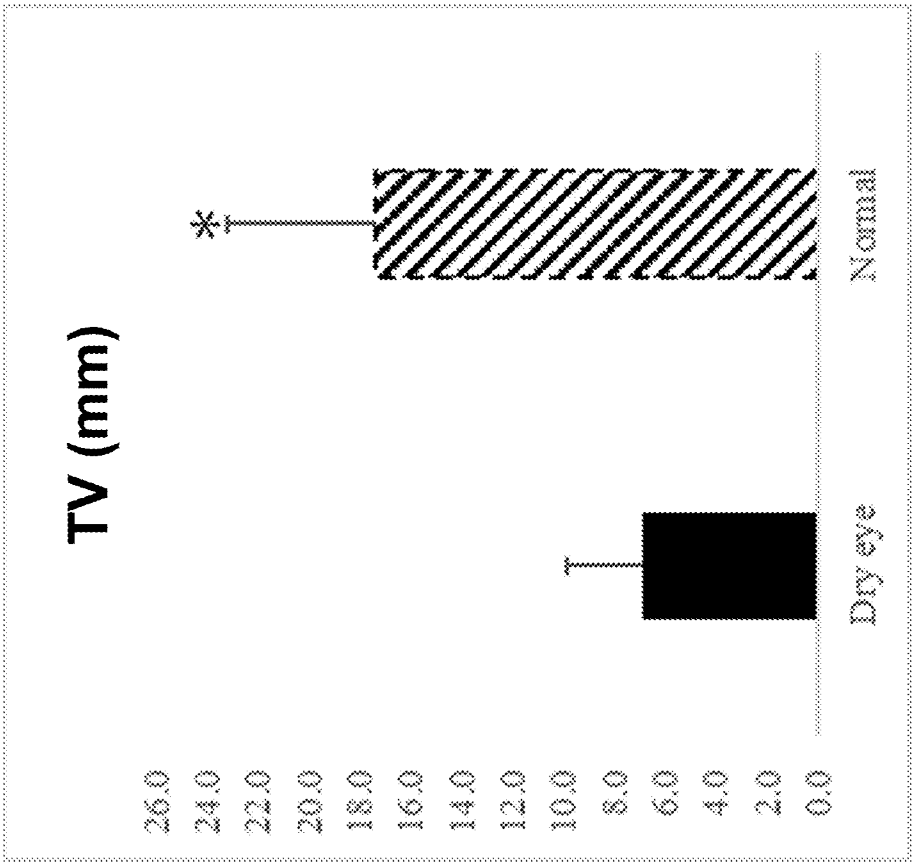
Figure 25D:
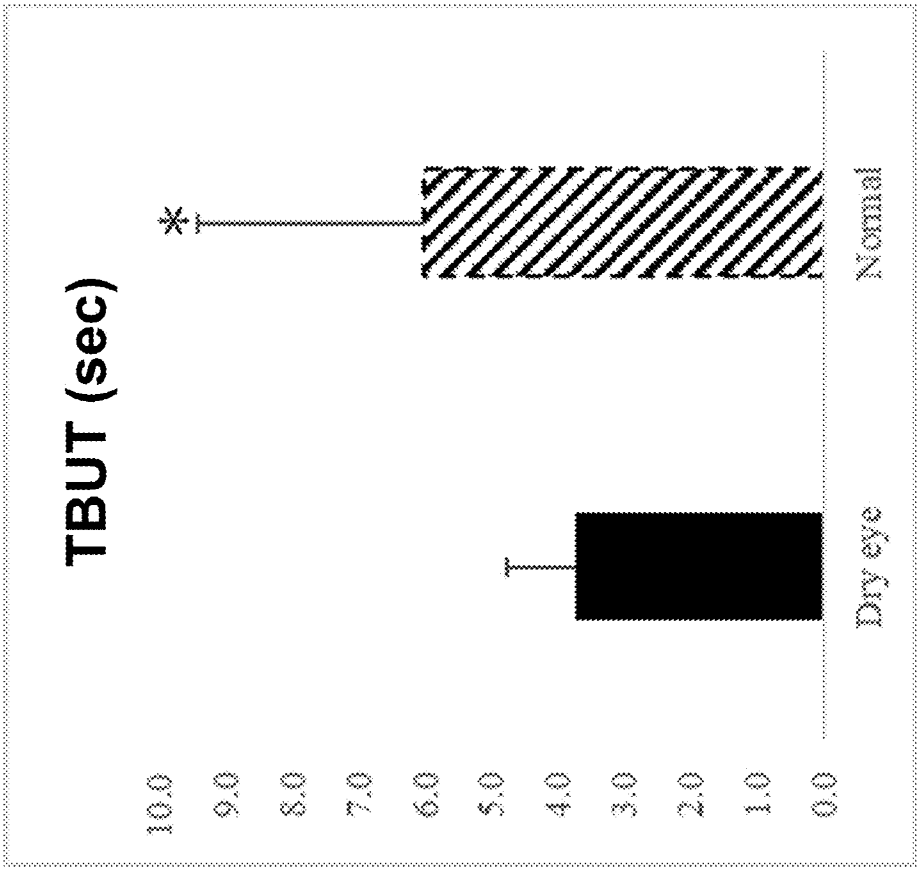
Figure 25E:
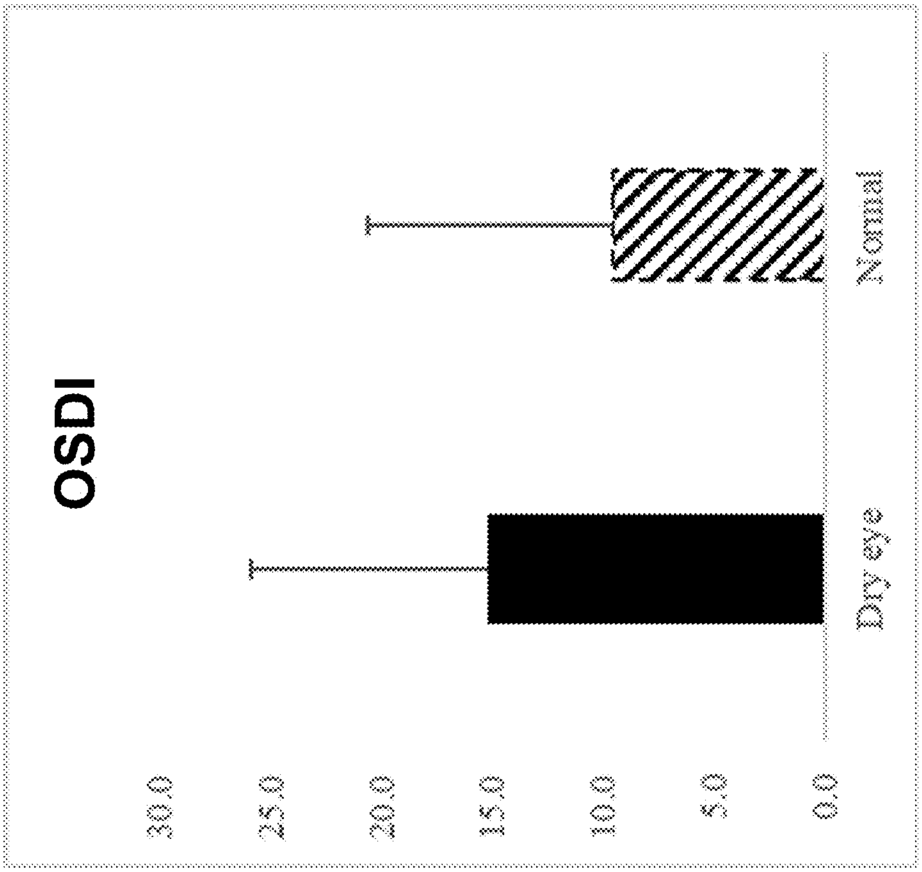
Figure 25F:
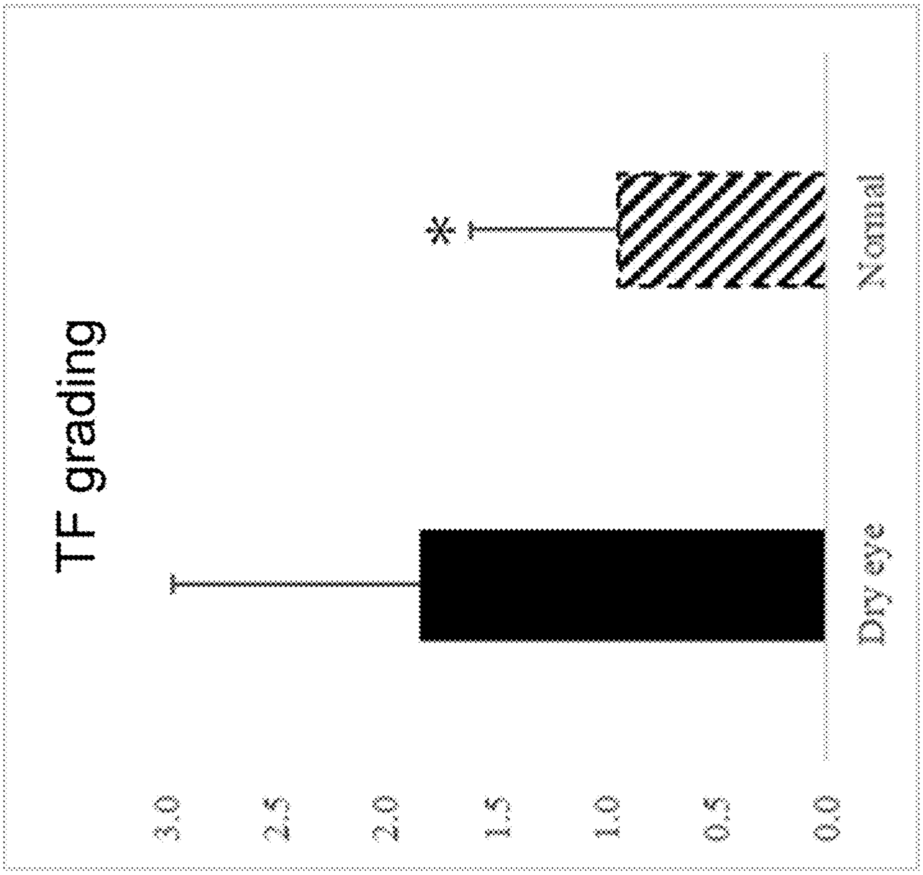

In ICR mice, all TF grades with 0.4% NaCl were equal or under 2, with 62.5% distributed between 0.5 and 1 (FIG. 24). For the C57BL/6J mice of the same age, all TF grades were also observed under 2 with 0.4% NaCl wash solution. These results indicated the advantage of using 0.4% NaCl as wash solution.

This improvement may extend the applicability of the TF test and may promote the use of TF test in clinical diagnosis.

Example 11

Tear Ferning Tests for Diagnosis of Dry Eye Diseases

This clinical trial was conducted in Jen-Ai Hospital in Dali, Taichung City, Taiwan. Subjects with or without dry eye disease were recruited by oral or poster introduction. The aim was to compare the tear ferning grades to examine whether the protocol can be used for dry eye diagnosis and provide clinical data for further research and development.

Inclusion and Exclusion Criteria

Subjects were diagnosed with dry eye, but without other obvious ocular pathologies such as keratopathy, cataract, vitreous degeneration, glaucoma, and retinopathies. The subjects aged between 20 to 65 years, without hypertension, diabetes, or other chronic diseases.

The subjects had Schirmer test results between 5-10 mm or TBUT less than 10 seconds, with OSDI scores more than 25. Vulnerable groups, or groups in loss of self-conscious and self-conducts, or with major diseases were excluded from this study:

The vulnerable groups included:

1. Women at pregnancy or having a fetus:
2. Prisoners:
3. Minorities:
4. Economic or educationally disadvantaged subjects:
5. Disabled individuals, such as cancer patients at terminal stage, blindness, or those terminally ill individuals using aided ventilation.

Number of Subjects

This study will include at least 20 subjects, 10 with dry eye subjects and 10 non-dry eye subjects, with equal gender distribution.

Subject Recruitments

The subjects will be recruited in Jen-Ai Hospital, Taichung, Taiwan. After oral introduction to the project, the subjects are recruited. The persons giving oral introduction are the principal investigator, ophthalmologists, nurses, and research assistants. The introduction took about 10 minutes, and informed consents were signed by the subjects.

Test Protocols

A. Intraocular pressure (IOP): indentation tonometer performed by clinical staff.
B. Tear volume (TV): also known as Schirmer test. A tear strip is inserted in the lower eye lid, in the fornix, and allowed to stay for 5 minutes. The wetted length in mm was used to assess teat volume.
C. Tear break up time (TBUT): a fluorescein eye drop eye drop is administered onto the eye surface. The subjects have natural eye blinks. The breakup time in seconds after the fluorescein layer on the ocular surface is recorded.
D. Ocular surface health assessment: a slip lamp is used to observe the health status after fluorescein staining
E. Tear collection and tear ferning: use a 0.4% NaCl wash solution to rinse and collect tear samples from the ocular surface. The tear samples were dropped onto a glass slide and allowed to dry and form ferning patterns.
F. Ocular surface disease index (OSDI): an OSDI questionnaire was used for the subjects to report their environmental conditions and sense of eye dryness. The answers were calculated to make a total score. The score can be used for correlations with other parameters.

Statistics

Descriptive statistics, independent and paired t-tests, and ANOVA analyses were used to examine significance. $p<0.05$ was considered significant.

TABLE 6

The data of the subjects in this clinical trial

| Dry eye | n = 15 Gender | Male n = 7 Age | Female n = 8 IOP(mmHg) | TV(mm) | TBUT(sec) | OSDI | TF grading |
|---|---|---|---|---|---|---|---|
| 01 | Female | 36 | 13.5 | 9.5 | 3.5 | 18.8 | 4.0 |
| 02 | Female | 32 | 20.8 | 8.0 | 2.5 | 12.5 | 3.3 |
| 03 | Male | 32 | 13.0 | 3.5 | 5.0 | 14.6 | 3.3 |
| 04 | Female | 22 | 15.0 | 4.0 | 4.0 | 20.8 | 3.3 |
| 06 | Male | 23 | 13.0 | 7.0 | 4.0 | 8.3 | 1.3 |
| 08 | Male | 22 | 15.8 | 11.0 | 5.0 | 27.5 | 1.8 |
| 09 | Male | 22 | 14.3 | 7.0 | 5.0 | 8.3 | 2.0 |
| 11 | Male | 22 | 16.8 | 4.5 | 3.0 | 6.3 | 0.3 |
| 12 | Female | 44 | 16.5 | 6.0 | 3.0 | 0 | 1.0 |
| 13 | Female | 35 | 15.0 | 12.5 | 4.5 | 8.3 | 1.3 |
| 14 | Female | 36 | 14.8 | 1.5 | 4.0 | 35.4 | 1.3 |
| 20 | Male | 20 | 18.0 | 5.5 | 2.0 | 30.0 | 1.5 |
| 21 | Male | 20 | 15.8 | 10.0 | 2.5 | 2.1 | 2.0 |
| 23 | Female | 35 | 12.8 | 6.0 | 5.0 | 25.0 | 0.3 |
| 24 | Female | 59 | 10.5 | 7.5 | 3.0 | 10.4 | 1.5 |
| | Mean | 31 | 15 | 7 | 4 | 15 | 2 |
| | SD | 10.9 | 2.5 | 3.0 | 1.0 | 10.6 | 1.1 |

| Normal | n = 9 Gender | Male n = 4 Age | Female n = 5 IOP(mmHg) | TV(mm) | TBUT(sec) | OSDI | TF grading |
|---|---|---|---|---|---|---|---|
| 7 | Male | 22 | 14.8 | 13.0 | 10.0 | 6.3 | 2.0 |
| 10 | Male | 21 | 19.5 | 24.5 | 8.0 | 12.5 | 1.3 |
| 15 | Female | 26 | 16.5 | 16.5 | 3.0 | 12.5 | 0.8 |
| 16 | Male | 36 | 13.3 | 14.0 | 10.0 | 5.0 | 0.3 |
| 17 | Female | 31 | 13.8 | 17.5 | 2.5 | 6.3 | 0.8 |

TABLE 6-continued

| The data of the subjects in this clinical trial | | | | | | | |
|---|---|---|---|---|---|---|---|
| 18 | Female | 29 | 16.0 | 10.0 | 10.0 | 36.4 | 0.5 |
| 19 | Female | 28 | 17.8 | 16.5 | 4.0 | 6.8 | 0.3 |
| 22 | Male | 20 | 11.8 | 15.0 | 3.5 | 0.0 | 2.0 |
| 25 | Male | 38 | 16.0 | 29.0 | 3.0 | 0.0 | 0.8 |
| | Mean | 28 | 15 | 17 | 6 | 10 | 1 |
| | SD | 6.4 | 2.4 | 5.9 | 3.4 | 11.0 | 0.7 |

*IOP: intraocular pressure, TV: tear volume, TBUT: tear film break up time, OSDI: ocular surface disease index. The TF gradings range between 0 to 4, at 0.5 intervals. Grading 0 represents healthy, and 4 represents sever dry eye status. The data were the average of both eyes.

Histograms of FIG. 25A-25F showing the data of the above Table 6. * indicates significant differences ($p<0.05$).

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes, and substitutions are intended in the foregoing disclosures. It will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

What is claimed is:

1. A method comprising:

drying a fluid sample from a subject to provide a dried fluid sample;

imaging the dried fluid sample to provide a sample image; and viewing and determining the sample image, if there is a ferning pattern representative of a biological condition of the subject in the image;

wherein analyzing the sample image is performed by using a Sophie-Kevin (SK) grading assembly to provide outputs indicating branching patterns of crystallization of the dried fluid sample for predicting the biological condition;

wherein the biological condition comprises Homeostatic Failure of Ocular Surface;

wherein the Homeostatic Failure of Ocular Surface comprises ocular surface diseases; wherein the ocular surface diseases comprise dry eyes and photokeratitis; and wherein the dry eyes comprise aqueous-deficient dry eye (ADDE), evaporative dry eye (EDE), and mucin-deficient dry eye.

2. The method according to claim 1, wherein analyzing the characteristic length or/and width of branching or/and trunk pattern segments of a crystalline pattern.

3. The method according to claim 1, wherein analyzing the characteristic for intersected at angles of a crystalline pattern.

4. The method according to claim 1, wherein analyzing the characteristic for the gaps between neighboring branches of a crystalline pattern.

5. The method according to claim 1, wherein analyzing the characteristic for shorter arms or/and square-like in shape of a crystalline pattern.

6. The method according to claim 1, wherein analyzing the characteristic with the presence of dense radiating snowflake patterns of a crystalline pattern.

7. The method according to claim 1, wherein analyzing the characteristic based on the percentage of non-crystal area.

8. The method according to claim 1, wherein analyzing the Ferning Grading Criteria defined into grade 0, 0.5, 1, 1.5, 2, 2.5, 3, 3.5 and 4.

9. The method according to claim 1, wherein the fluid sample was collected with a wash solution containing 0.4%-0.9% NaCl with the pH value maintained at 5.5-7.5±0.2.

10. The method according to claim 1, wherein the fluid sample comprises tears.

* * * * *